United States Patent
Polotsky et al.

(10) Patent No.: US 11,229,614 B2
(45) Date of Patent: Jan. 25, 2022

(54) SUPRAMOLECULAR HYDROGEL APPLICATIONS TO THE CAROTID BODIES TO TREAT HYPERTENSION AND SLEEP APNEA IN OBESITY

(71) Applicant: THE JOHNS HOPKINS UNIVERSITY, Baltimore, MD (US)

(72) Inventors: Vsevolod Polotsky, Pikesville, MD (US); Honggang Cui, Lutherville, MD (US); Roxana Elena Mitrut, Plainsboro, NJ (US); Mi-kyung Shin, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/955,626

(22) PCT Filed: Dec. 19, 2018

(86) PCT No.: PCT/US2018/066371
§ 371 (c)(1),
(2) Date: Jun. 18, 2020

(87) PCT Pub. No.: WO2019/126256
PCT Pub. Date: Jun. 27, 2019

(65) Prior Publication Data
US 2021/0052520 A1 Feb. 25, 2021

Related U.S. Application Data

(60) Provisional application No. 62/607,363, filed on Dec. 19, 2017.

(51) Int. Cl.
| | | |
|---|---|---|
| A61K 31/137 | (2006.01) | |
| A61K 47/55 | (2017.01) | |
| A61K 47/64 | (2017.01) | |
| A61K 47/54 | (2017.01) | |
| A61P 9/12 | (2006.01) | |
| A61K 9/06 | (2006.01) | |
| A61K 9/70 | (2006.01) | |
| A61K 31/05 | (2006.01) | |
| A61K 31/122 | (2006.01) | |
| A61K 31/131 | (2006.01) | |
| A61K 31/133 | (2006.01) | |
| A61K 31/155 | (2006.01) | |
| A61K 31/352 | (2006.01) | |
| A61K 31/405 | (2006.01) | |
| A61K 31/4174 | (2006.01) | |
| A61K 31/4184 | (2006.01) | |
| A61K 31/428 | (2006.01) | |
| A61K 31/444 | (2006.01) | |
| A61K 31/4709 | (2006.01) | |
| A61K 31/506 | (2006.01) | |
| A61K 31/69 | (2006.01) | |

(52) U.S. Cl.
CPC ............ *A61K 31/137* (2013.01); *A61K 9/06* (2013.01); *A61K 9/70* (2013.01); *A61K 31/05* (2013.01); *A61K 31/122* (2013.01); *A61K 31/131* (2013.01); *A61K 31/133* (2013.01); *A61K 31/155* (2013.01); *A61K 31/352* (2013.01); *A61K 31/405* (2013.01); *A61K 31/4174* (2013.01); *A61K 31/4184* (2013.01); *A61K 31/428* (2013.01); *A61K 31/444* (2013.01); *A61K 31/4709* (2013.01); *A61K 31/506* (2013.01); *A61K 31/69* (2013.01); *A61K 47/54* (2017.08); *A61K 47/55* (2017.08); *A61K 47/64* (2017.08); *A61P 9/12* (2018.01)

(58) Field of Classification Search
CPC ...................................................... A61K 31/137
USPC ......................................................... 514/64
See application file for complete search history.

(56) References Cited

U.S. PATENT DOCUMENTS

2010/0159508 A1  6/2010  Yang et al.

OTHER PUBLICATIONS

Qin, British Journal of Pharmacology (2013) 168 1294-1312.*
Qin, X., et al., "Sphingosine and FTY720 are potent inhibitors of the transient receptor potential melastatin 7 (TRPM7) channels" British Journal of Pharmacology (2013) 168 1294-1312.
Shin, M., "Leptin increases blood pressure acting via transient receptor potential (TRP) channels in the carotid body" The FASEB Journal 2017, T.31, No. 1, supplement, p. 1025.2-1025.2.

* cited by examiner

*Primary Examiner* — Nizal S Chandrakumar
(74) *Attorney, Agent, or Firm* — Casimir Jones, S.C.; Thomas A. Isenbarger

(57) ABSTRACT

The present invention provides compositions and methods for treating hypertension and obstructive sleep apnea utilizing hydrogel compositions comprising drug amphiphiles with TRPM 7 antagonists for use in a subject, including use on the carotid body of a subject.

4 Claims, 12 Drawing Sheets
Specification includes a Sequence Listing.

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Phe Phe Glu Glu
1

<210> SEQ ID NO 2
<211> LENGTH: 5
<212> TYPE: PRT
<213> ORGANISM: Artificial Sequence
<220> FEATURE:
<223> OTHER INFORMATION: synthetic sequence

<400> SEQUENCE: 2

Gly Val Val Gln Gln
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic sequence
```

```
<400> SEQUENCE: 3

Phe Phe Phe Glu Glu Glu
1               5

<210> SEQ ID NO 4
<211> LENGTH: 4
<212> TYPE: PRT
<213> ORGANISM: Artificial Sequence
<220> FEATURE:
<223> OTHER INFORMATION: synthetic sequence

<400> SEQUENCE: 4

Phe Glu Phe Glu
1

<210> SEQ ID NO 5
<211> LENGTH: 6
<212> TYPE: PRT
<213> ORGANISM: Artificial Sequence
<220> FEATURE:
<223> OTHER INFORMATION: synthetic sequence

<400> SEQUENCE: 5

Phe Glu Phe Glu Phe Glu
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic sequence

<400> SEQUENCE: 6

Val Val Val Glu Glu
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic sequence

<400> SEQUENCE: 7

Lys Val Val Val Glu Glu
1               5
```

SUPRAMOLECULAR HYDROGEL APPLICATIONS TO THE CAROTID BODIES TO TREAT HYPERTENSION AND SLEEP APNEA IN OBESITY

REFERENCE TO RELATED APPLICATIONS

This application is a 35 U.S.C. § 371 U.S. national entry of International Application PCT/US2018/066371, having an international filing date of Dec. 19, 2018, which claims the benefit of U.S. Provisional Patent Application No. 62/607,363, filed on Dec. 19, 2017, both of which are hereby incorporated by reference for all purposes as if fully set forth herein.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Dec. 18, 2018, is named P15001-02_ST25.txt and is 1,399 bytes in size.

BACKGROUND OF THE INVENTION

Obesity is a highly prevalent condition observed in 34.9% of US adults. Obesity leads to cardiovascular disease1 increasing mortality by 2-3 fold. Excessive adiposity causes multiple complications including obstructive sleep apnea (OSA) and hypertension, which greatly contribute to the cardiovascular risk. There is no pharmacotherapy for OSA. The high prevalence of hypertension and resistant hypertension in obesity has been linked to SNS activation related to obesity per se and to comorbid OSA. However, CPAP improves control of blood pressure only in 25-30% of adherent patients. Moreover, greater than 20% of all hypertensive patients adherent to therapy are resistant to the optimal medical regimen with obesity as a key risk factor.

Leptin is a potent stimulator of the sympathetic nervous system (SNS), and hyperleptinemia is associated with hypertension in obese humans and rodents. Moreover, leptin increases the hypoxic ventilatory response (HVR) resulting in respiratory instability exacerbating comorbid OSA. OSA leads to further progression of hypertension. Thus, leptin contributes to the pathogenesis of hypertension and OSA in obesity. Carotid bodies (CB) are major peripheral hypoxia sensors transmitting chemosensory input via the carotid sinus nerve (CSN) to the medullary centers, which results in acute hyperventilation in response to hypoxia and the activation of the SNS. Obesity and comorbid OSA sensitize the CB.

Thus, treatment of OSA and hypertension in obesity poses significant therapeutic challenges and new treatment modalities are urgently needed.

SUMMARY OF THE INVENTION

In accordance with some embodiments, the present inventors now show that (1) leptin activates CB via non-selective cation transient receptor potential channels (TRP); (2) that hypoxia-sensitive transient receptor potential melastatin 7 (TRPM7) expression in CB is transcriptionally regulated by leptin; (3) leptin induces hypertension and this effect is abolished by CSN denervation and TRPM7 blockers; (4) leptin regulates the HVR and this effect is abolished by TRPM7 blockers administered systemically. Most importantly, FTY720 or fingolimod, an FDA approved drug to treat multiple sclerosis and a potent TRPM7 blocker, abolished leptin-induced hypertension when administered to CB locally.

In accordance with an embodiment, the present invention provides a composition comprising a drug amphiphile comprising a TRPM7 receptor antagonist.

In accordance with another embodiment, the present invention provides a pharmaceutical composition comprising a drug amphiphile comprising a TRPM7 receptor antagonist and a pharmaceutically acceptable carrier.

In accordance with yet another embodiment, the present invention provides a pharmaceutical composition comprising a drug amphiphile comprising a TRPM7 receptor antagonist, a pharmaceutically acceptable carrier and at least one additional biologically active agent.

In accordance with an embodiment, the present invention provides a method for treating obesity induced hypertension in a subject suffering therefrom, comprising administering to the subject, an effective amount of a composition comprising a drug amphiphile comprising a TRPM7 receptor antagonist.

In accordance with another embodiment, the present invention provides a method for treating obesity induced hypertension in a subject suffering therefrom, comprising administering to the subject, an effective amount of a pharmaceutical composition comprising a drug amphiphile comprising a TRPM7 receptor antagonist and a pharmaceutically acceptable carrier.

In accordance with yet another embodiment, the present invention provides a method for treating obesity induced hypertension in a subject suffering therefrom, comprising administering to the carotid body of the subject, an effective amount of a composition comprising a drug amphiphile comprising a TRPM7 receptor antagonist.

In accordance with a further embodiment, the present invention provides a method for treating obesity induced hypertension in a subject suffering therefrom, comprising administering to the carotid body of the subject, an effective amount of a pharmaceutical composition comprising a drug amphiphile comprising a TRPM7 receptor antagonist and a pharmaceutically acceptable carrier.

In accordance with an embodiment, the present invention provides a method for treating obstructive sleep apnea in a subject suffering therefrom, comprising administering to the subject, an effective amount of a composition comprising a drug amphiphile comprising a TRPM7 receptor antagonist.

In accordance with another embodiment, the present invention provides a method for treating obstructive sleep apnea in a subject suffering therefrom, comprising administering to the subject, an effective amount of a pharmaceutical composition comprising a drug amphiphile comprising a TRPM7 receptor antagonist and a pharmaceutically acceptable carrier.

In accordance with yet another embodiment, the present invention provides a method for treating obstructive sleep apnea in a subject suffering therefrom, comprising administering to the carotid body of the subject, an effective amount of a composition comprising a drug amphiphile comprising a TRPM7 receptor antagonist.

In accordance with a further embodiment, the present invention provides a method for treating obstructive sleep apnea in a subject suffering therefrom, comprising administering to the carotid body of the subject, an effective amount of a pharmaceutical composition comprising a drug amphiphile comprising a TRPM7 receptor antagonist and a pharmaceutically acceptable carrier.

DETAILED DESCRIPTION OF THE INVENTION

Figure 1:
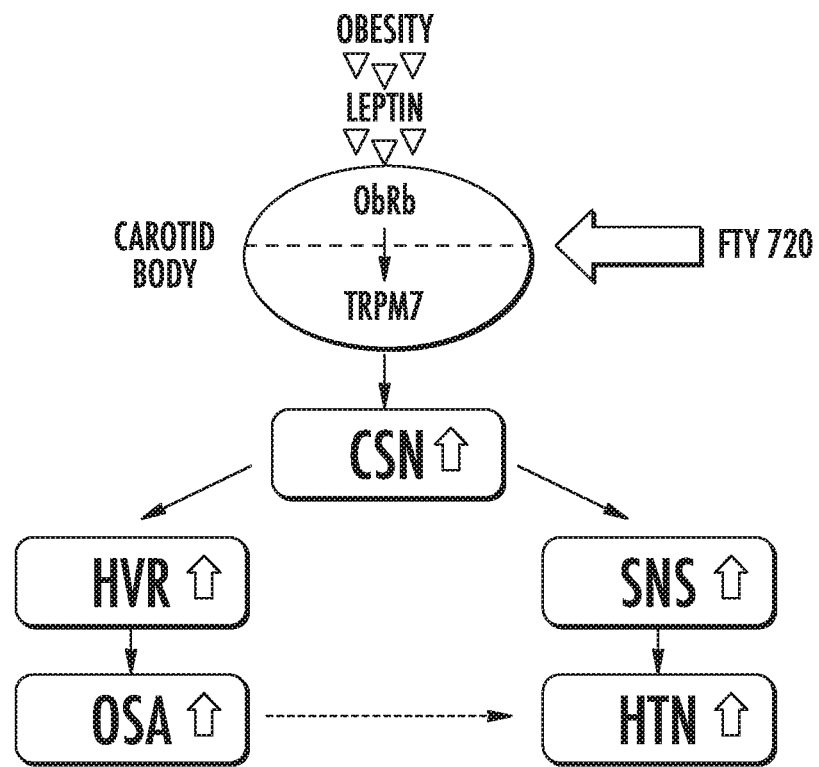
FIG. 1 illustrates the basic concepts regarding the mechanism of hypertension and obstructive sleep apnea.
Figure 2:
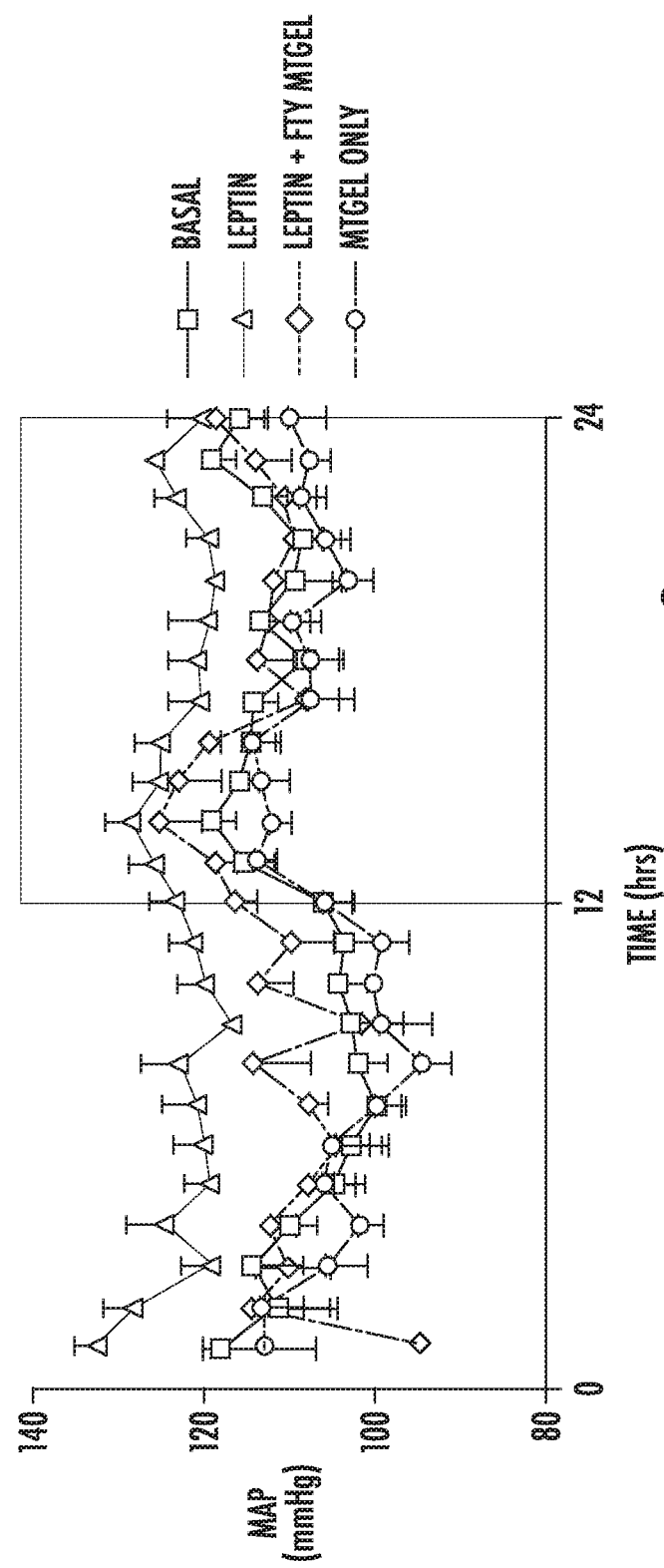
FIG. 2 shows FTY720 application in Matrigel at 0.3 mg/kg/day to CB abolished leptin-induced hypertension.

The present invention provides herein a new monodisperse, amphiphilic prodrug—that can spontaneously associate into discrete, stable hydrogels with supramolecular nanostructures. These nanofiber hydrogels follow similar principles as those first developed in International Patent Publication No. WO 2014/066002, and incorporated by reference herein. The very nature of the molecular design ensures that a fixed and tunable drug loading can be achieved, without the use of any additional carriers or matrices. The present invention discloses the use of these nanofiber hydrogels for local treatment of the carotid body in a subject to treat hypertension, obstructive sleep apnea, and related disorders.

In order to imbue these properties upon a drug or biologically active agent for brain-related diseases, a peptide or oligopeptide with overall hydrophilicity (Pep) is biodegradably linked with the drug or biologically active agent. The peptide or oligopeptide chosen increases the aqueous solubility of the drug or biologically active agent and can promote the formation of well-defined one-dimensional nanostructure architectures including, but not limited to, cylindrical micelles, hollow nanotubes, filaments, fibrils, twisted ribbons, helical ribbons, nanobelts, nanofibers, through preferred secondary structure formation, e.g. beta sheet, alpha helix, poly proline type-II helix, and beta turns. In some embodiments, the nanofiber hydrogels of the present invention are capable of forming three dimensional nanofiber networks and hydrogels in aqueous conditions.

The nanofiber hydrogel used in the drug amphiphile compositions and methods of the present invention provide a sustained release local drug delivery system.

In accordance with an embodiment, the present invention provides a nanofiber hydrogel drug amphiphile composition comprising 1 to 4 drug or biologically active agent moieties (D) for brain diseases conjugated to a hydrophilic peptide composition (Pep).

In some embodiments, Pep is a peptide composition having the amino acid sequence $B_n(T)_z$, wherein $B_n$ is an amino acid, of n=0 to 12 amino acids, which can be the same or different, and T is a peptide of z=1 to 15 peptides, with biologically relevant properties including, but not limited to, tumor targeting, tissue penetrating, cell penetrating, apoptotic) or capable of binding to known cellular epitopes, such as integrins or cancer cell receptors.

In accordance with one or more embodiments, D can be conjugated to Pep (D-Pep) through the use of a chemical linker (L) in the form D-L-Pep. L is 0 to 4 biodegradable linkers. The linker can be an ester bond, amide bond, carbonate bond, hydrozone, disulfide bond, a diacid, or any amino acid, such as Gly, or one with a side chain having a free amino, carboxyl or thiol group, or a short peptide that can be specifically cleaved by a particular enzyme or proteinase.

In accordance with an embodiment, the biodegradable linkers of the present invention include (4-(pyridin-2-yldisulfanyl)butanoate) (buSS). The buSS linker has a disulfide moiety that allows it to be reductively cleaved primarily intracellularly by glutathione. In other embodiments, the linker can be disulfanylcarbonate (etSS). In other embodiments, the linker can be an amino acid such as Glu or Gln.

In accordance with another embodiment, D can be conjugated to Pep (D-Pep) where Pep is linked to a hydrophobic moiety (H). The hydrophobic moiety can be, in some embodiments, an alkyl chain (D-H-Pep). Examples of hydrophobic moieties are alkyl chains of $C_8$ to $C_{22}$ in length.

In accordance with an embodiment, the present invention provides a method of local administration of one or more biologically active agents to a subject comprising in situ application of a drug amphiphile composition comprising D-Pep and/or D-L-Pep and/or D-H-Pep to the site of interest.

In accordance with still another embodiment, D can be conjugated to Pep (D-Pep) where Pep is linked to a hydrophobic moiety (H) and to a linker (L) in the same molecule. The hydrophobic moiety can be, in some embodiments, an alkyl chain conjugated to the Pep portion of the molecule. In other embodiments, both the drug D and hydrophobic moiety (H) are conjugated to Pep via a linker L.

In accordance with an embodiment, the present invention provides a method of local administration of one or more biologically active agents to a subject comprising in situ injection of a drug amphiphile composition comprising a mixture comprising D-Pep and/or D-L-Pep and/or D-H-Pep, and upon contact with body fluids at body temperature, the composition is capable of undergoing a change from solution state to nanofiber gelation state.

In accordance with an embodiment, the delivered nanofiber hydrogels can sustainably release the encapsulated bioactive agents over a long period of time.

In accordance with an embodiment, the nanofiber hydrogel drug amphiphiles contain a fixed loading of the biological agents which is tunable and precisely defined by the molecular design, and will not require additional matrices/hydrogels for the delivery of the biological agents.

In accordance with an embodiment, the nanofiber form enables diffusion across larger areas relative to individual molecules and avoids capillary loss.

In some preferred embodiments, the compositions of the present invention are prepared as a dry powder and then come in contact with aqueous solutions, for example, such as physiological buffers or tissue fluids such as blood or lymph, and will spontaneously form aqueous nanofiber hydrogels. In alternative embodiments, the compositions of the present invention can be formulated in a viscous liquid or vitrigel form and then are applied to the tissues of interest to become aqueous nanofiber hydrogels in the presence of body heat.

It is contemplated that the other hydrophobic molecules can be used in the D-Pep molecules of the present invention. For example, other hydrophobic molecules such as steroids, other conjugated ring containing molecules, and hydrophobic drugs can be used.

As used herein, the term "hydrophobic" biologically active agents or drug molecules describes a heterogeneous group of molecules that exhibit poor solubility in water but that are typically, but certainly not always, soluble in various organic solvents. Often, the terms slightly soluble (1-10 mg/ml), very slightly soluble (0.1-1 mg/ml), and practically insoluble (<0.1 mg/ml) are used to categorize such substances. Drugs such as steroids and many anticancer drugs are important classes of poorly water-soluble drugs; however, their water solubility varies over at least two orders of magnitudes. Typically, such molecules require secondary solubilizers such as carrier molecules, liposomes, polymers, or macrocyclic molecules such as cyclodextrins to help the hydrophobic drug molecules dissolve in aqueous solutions necessary for drug delivery in vivo. Other types of hydrophobic drugs show even a lower aqueous solubility of only a few ng/ml. Since insufficient solubility commonly accompanies undesired pharmacokinetic properties, the high-throughput screening of kinetic and thermodynamic solubility as well as the prediction of solubility is of major importance in discovery (lead identification and optimization) and development.

The compositions of the present invention harnesses the hydrophobic properties of FTY720 to drive the formation of fingolimod-based filamentous nanostructures through the creation of drug amphiphiles (DAs).

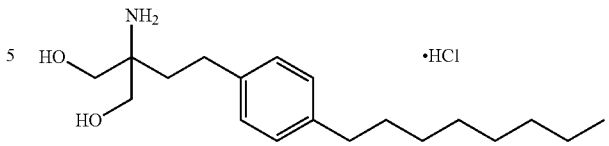

FTY720 (2-Amino-2-[2-(4-octyl-phenyl)-ethyl]-propane-1,3-diol hydrochloride) (fingolimod) is a derivative of ISP-1 (myriocin), a fungal metabolite of the Chinese herb Iscaria sinclarii as well as a structural analog of sphingosine. It is a novel immune modulator that prolongs allograft transplant survival in numerous models by inhibiting lymphocyte emigration from lymphoid organs. FTY720 is phosphorylated by sphingosine kinase, which then acts as a potent agonist at four of the sphingosine-1-phosphate (SIP) receptors (S1P1, S1P3, S1P4, and S1P5). Down-regulation of S1P1 receptors on T and B lymphocytes by FTY720 results in defective egress of these cells from spleen, lymph nodes, and Peyer's patch. FTY720 also enhances the activity of the sphingosine transporter Abcb1 and the leukotriene C4 transporter Abcc1 and inhibits cytosolic phospholipase A2 activity.

The present inventors have previously demonstrated that rationally designed camptothecin (CPT) DAs can spontaneously associate into supramolecular nanofibers of tens of micrometers long when dispersed in aqueous solutions. These molecules are the subject of the following U.S. Pat. No. 9,180,203, and U.S. patent application Ser. No. 14/934,660, and incorporated by reference herein as if set forth in their entirety.

The present inventors previously discovered that a solution containing self-assembling CPT drug amphiphiles can be directly delivered into the tumor site, and then forms a gel immediately upon contact with the brain without noticeable immunogenicity.

In accordance with an embodiment, the delivered nanofiber hydrogels of the present invention can sustainably release the encapsulated bioactive agents over a long period of time.

In accordance with an embodiment, the present invention provides a composition comprising a drug amphiphile comprising a TRPM7 receptor antagonist.

In some embodiments, the TRPM7 antagonist is selected from the group consisting of: spermine, 2-aminoethyl diphenylborinate (2-APB), SKF-96365 (1-[b-[3-(4-methoxyphenyl)propoxy]-4-methoxyphenethyl]-1H-imidazole, HCl), Nafamostat (4-[(Aminoiminomethyl)amino]benzoic acid 6-(aminoiminomethyl)-2-naphthalenyl ester dimethanesulfonate), Carvacrol (5-isopropyl-2-methylphenol); NDGA (nordihydroguaiaretic acid), AA861 (2-(12-hydroxydodeca-5,10-diynyl)-3,5,6-trimethyl-p-benzoquinone, 2,3,5-trimethyl-6-(12-hydroxy-5,10-dodecadiynyl)-1,4-benzoquinone), MK886 (2-(12-hydroxydodeca-5,10-diynyl)-3,5,6-trimethyl-p-benzoquinone, 2,3,5-trimethyl-6-(12-hydroxy-5,10-dodecadiynyl)-1,4-benzoquinone), Waixenicin A (2E,5S)-5-[(1R,4aS,11aR)-1-Acetoxy-7-methyl-11-methylene-1,4a,5,6,9,10,11,11a-octahydrocyclonona[c]pyran-4-yl]-2-methyl-2-pentene-1,5-diyl diacetate), NS8593 (N-[(1R)-1,2,3,4-Tetrahydro-1-naphthalenyl]-1H-Benzimidazol-2-amine), Quinine, CyPPA (N-Cyclohexyl-N-[2-(3,5-dimethyl-pyrazol-1-yl)-6-methyl-4-pyrimidinamine), Dequalinium (1-[10-(4-amino-2-methylquinolin-1-ium-1-yl)decyl]-2-methylquinolin-1-ium-4-amine), SKA31

(Naphtho[1,2-d]thiazol-2-ylamine), UCL 1684 (6,12,19,20, 25,26-hexahydro-5,27:13,18:21,24-Trietheno-11,7-metheno-7H-dibenzo[b,m][1,5,12,16]tetraazacyclotricosine), sphingosine, and FTY720.

In some embodiments, the TRPM7 antagonist is FTY720 or derivative thereof.

In an embodiment the drug amphiphile comprises FTY720 linked via a biodegradable linker to a hydrophilic tetrapeptide.

In a specific embodiment, the drug amphiphile comprises FTY720 linked via a biodegradable linker to the peptide FFEE (SEQ ID NO: 1) and shown as formula 1:

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thie- (1)

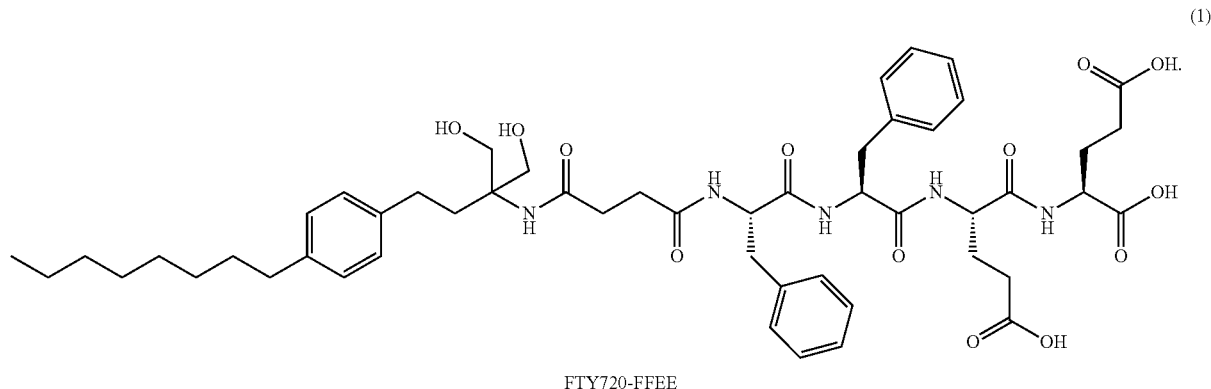 [SMILES: CCCCCCCCc1ccc(CCC(CO)(CO)NC(=O)CCC(=O)N[C@@H](Cc2ccccc2)C(=O)N[C@@H](Cc2ccccc2)C(=O)N[C@@H](CCC(=O)O)C(=O)N[C@@H](CCC(=O)O)C(=O)O)cc1]

FTY720-FFEE

In some embodiments, the drug amphiphile peptide moiety can be VVVEE (SEQ ID NO: 6).

In some embodiments, the drug amphiphile peptide moiety can be KVVVEE (SEQ ID NO: 7)

In some embodiments, the drug amphiphile peptide moiety can be GVVQQ (SEQ ID NO: 2).

In some embodiments, the drug amphiphile peptide moiety can be FFFEEE (SEQ ID NO: 3), FEFE (SEQ ID NO: 4), and FEFEFE (SEQ ID NO: 5), for example.

In some embodiments, Gly can also be used as a linker.

Figure 4:
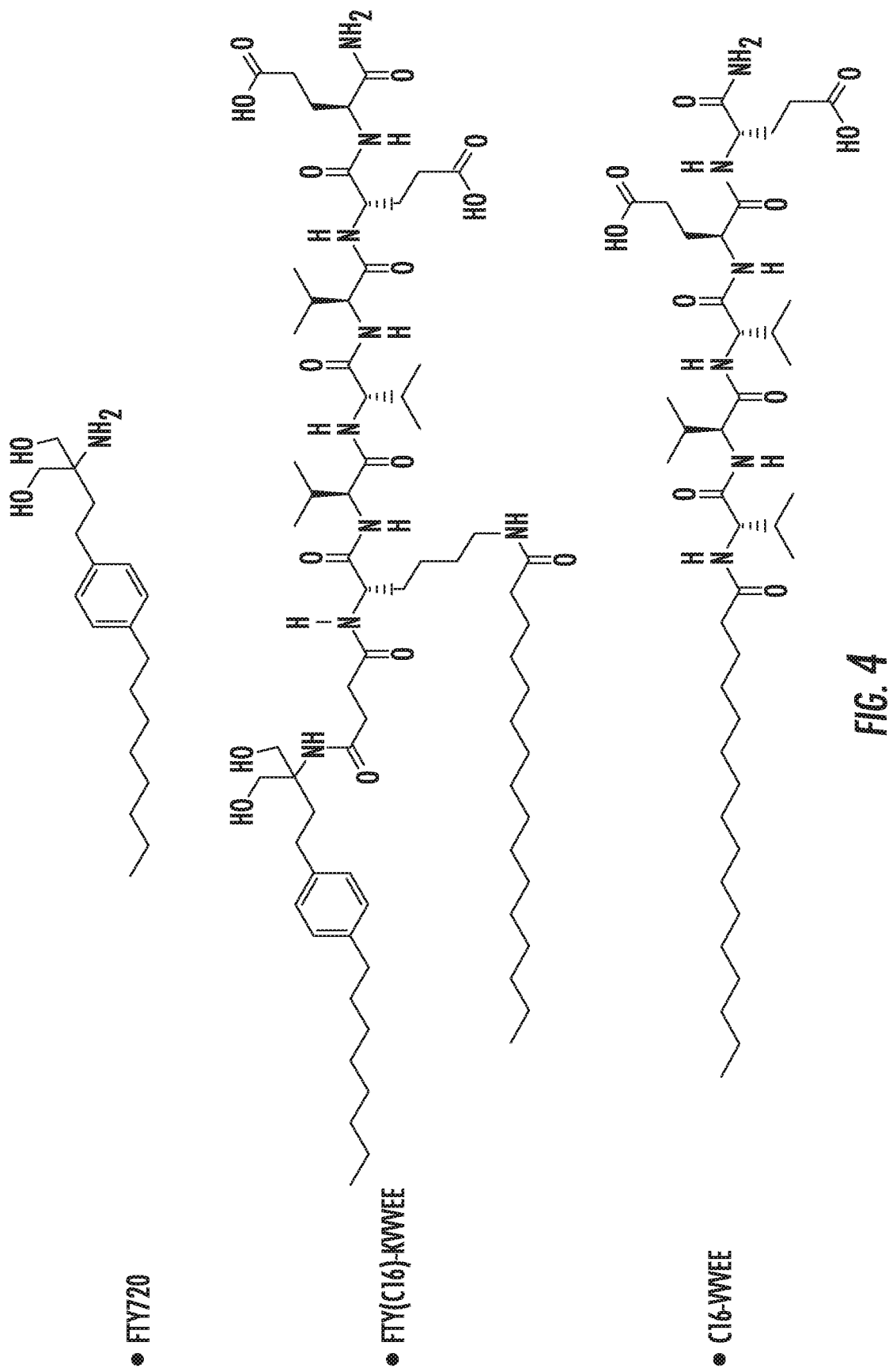
FIG. 4 depicts chemical structures of some TRPM7 receptor antagonists and drug amphiphiles of the present invention. Shown is FTY720, FTY720 co-assembled with a amphiphile comprising the peptide KVVVEE and a $C_{16}$ hydrocarbon tail, and the drug amphiphile VVVEE conjugated to a $C_{16}$ hydrocarbon tail.
Figure 5:
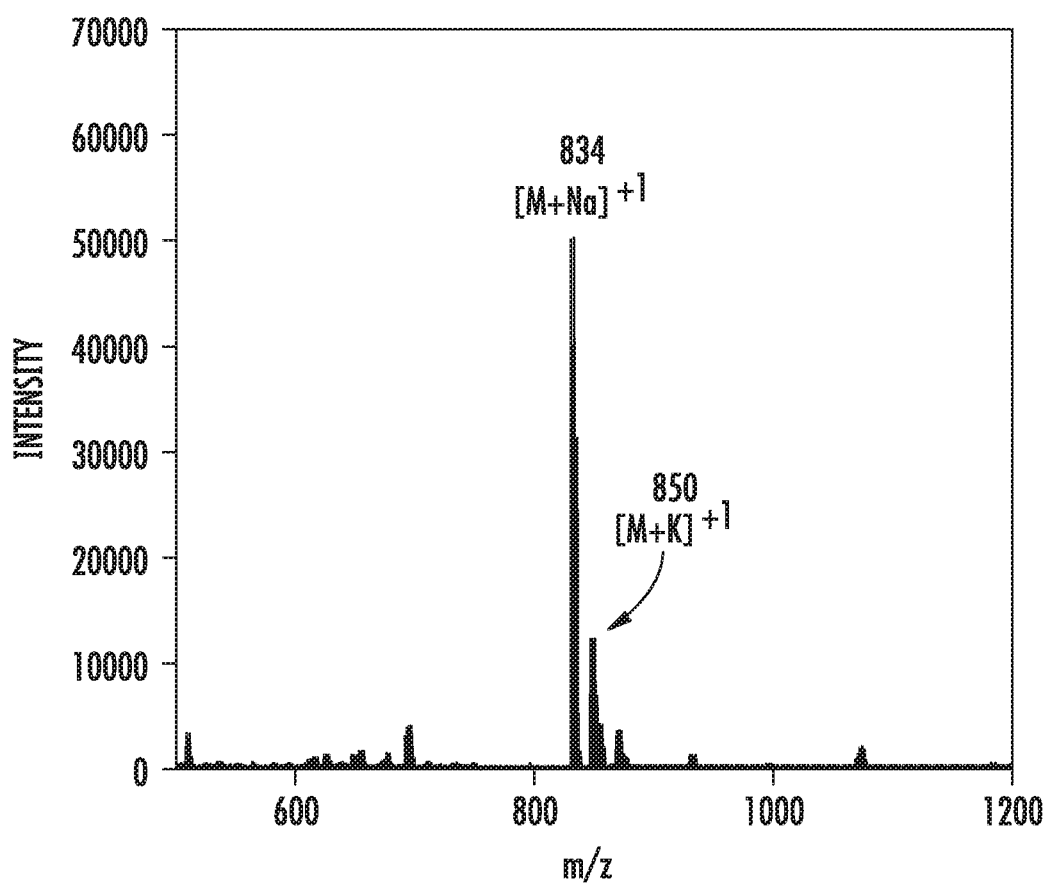
FIG. 5 is a graph of the MALDI mass spectrum data for C16-VVVEE peptide. M=811 g/mol.
Figure 6A:
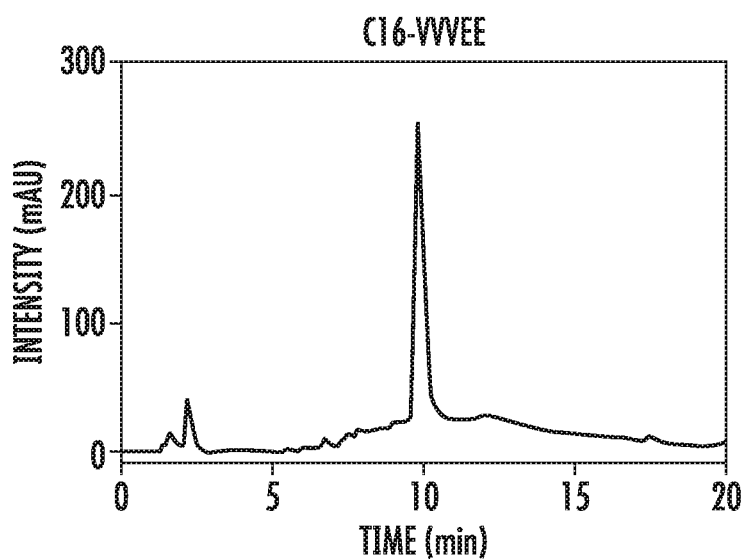
FIGS. 6A-6B are high performance liquid chromatography (HPLC) chromatographs depicting 6A) C16-VVVEE peptide and 6B) FTY720 showing single peak purity.
Figure 6B:
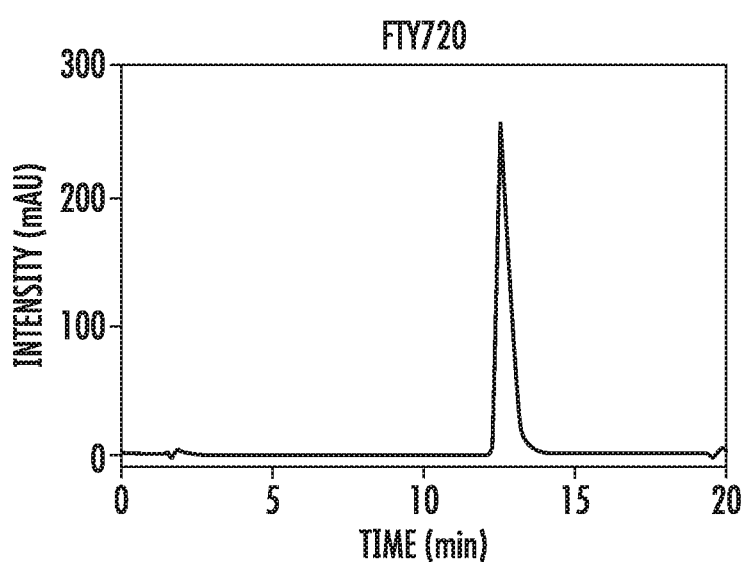
Figure 7:
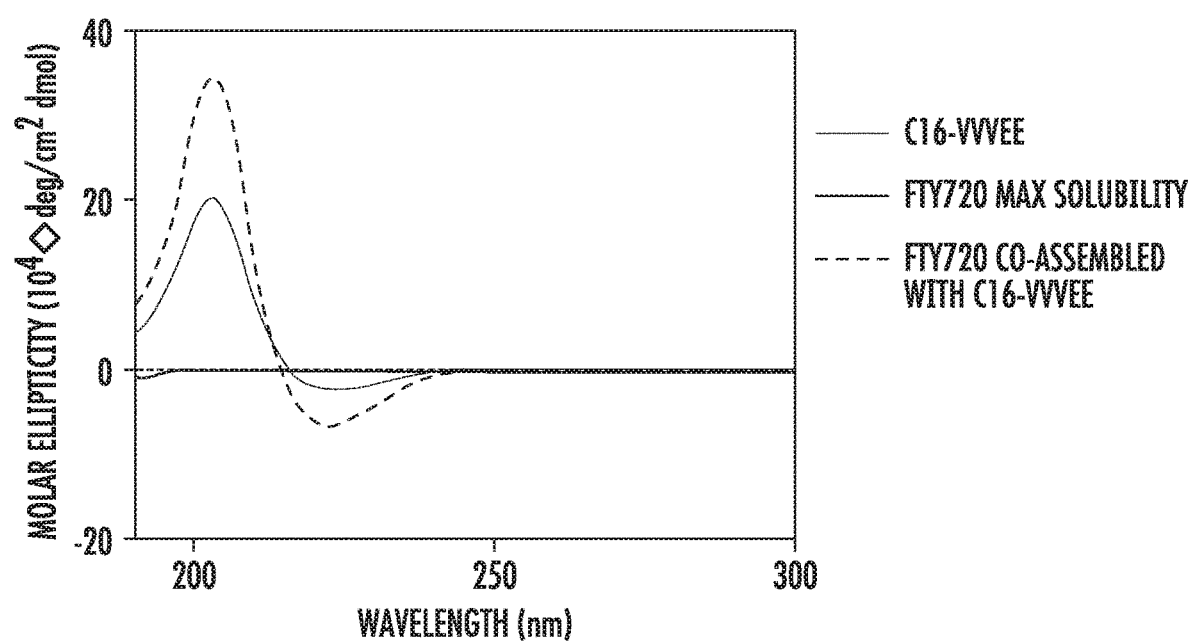
FIG. 7 depicts Circular Dichroism data of C16-VVVEE, FTY720, and FTY720 co-assembled with C16-VVVEE. Solutions were diluted to 100 µM for data collection. FTY720, prepared at 81 µM at pH 7.4 (maximum solubility at this pH), does not have secondary structure when prepared alone. C16-VVVEE, self-assembled at 15 mM, has secondary structure displays beta sheet characteristics, with the characteristic peaks present (negative peak at 220 nm and a positive peak at 200 nm, red shifted from 190 nm). When 1 mM FTY720 is co-assembled with 15 mM C16-VVVEE, secondary structure displays beta sheet characteristics with intensified peaks.
Figure 8:
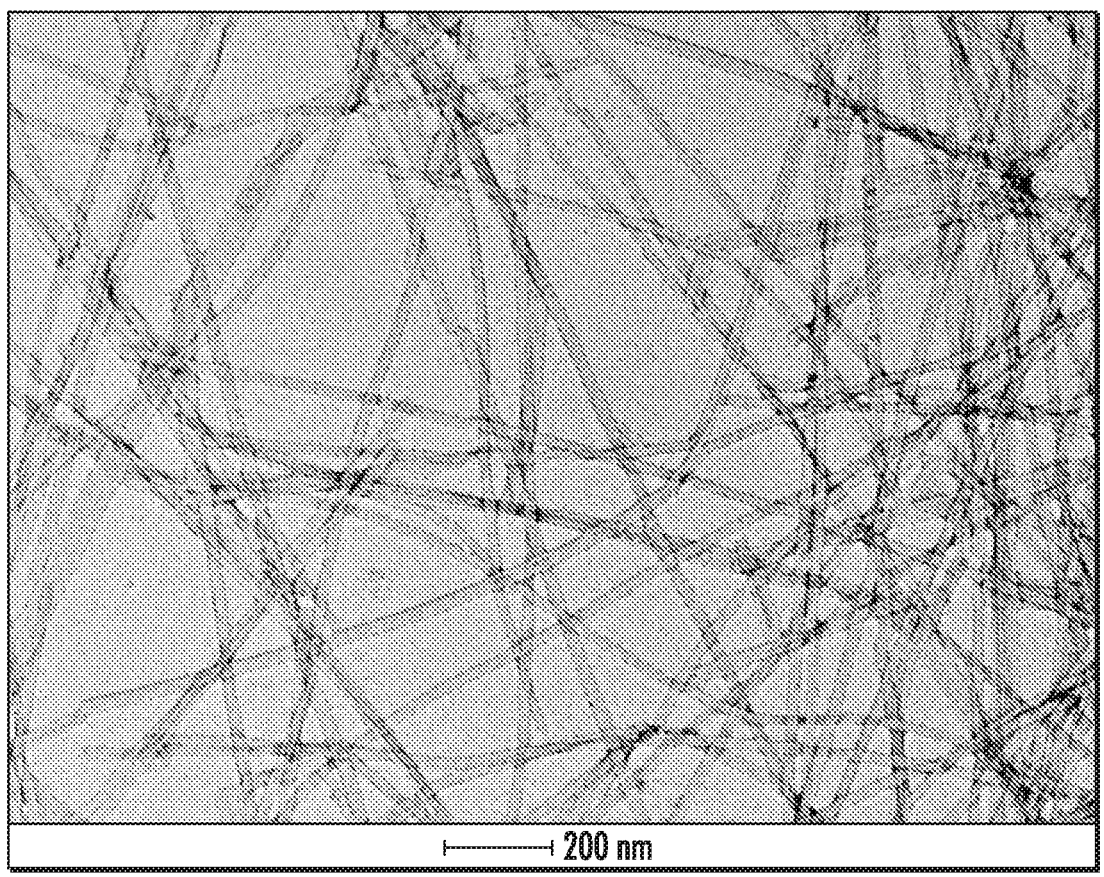
FIG. 8 is a transmission electron microscopy (TEM) photograph of self-assembled C16-VVVEE. The solution was prepared at 15 mM and pH 7.4, and aged overnight. TEM images show uniform nanobelts.
Figure 9:
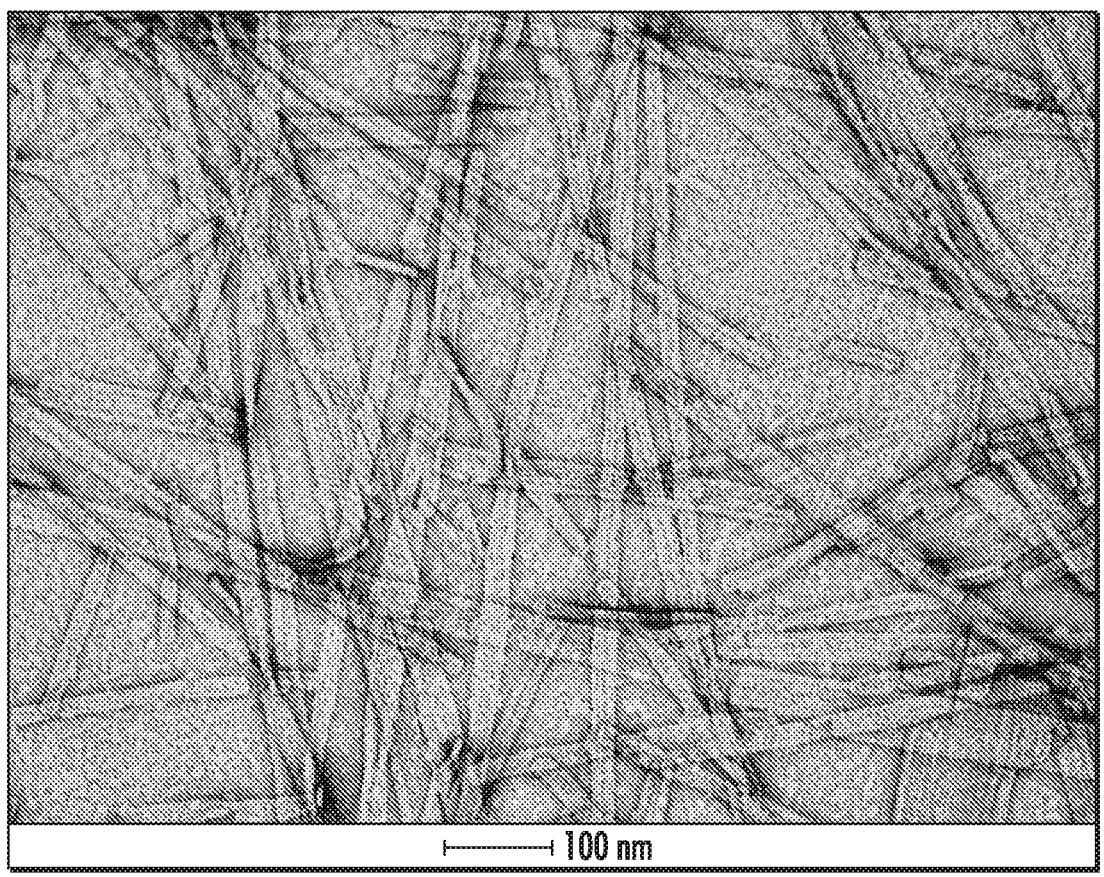
FIG. 9 is a TEM photograph of FTY720 co-assembled with C16-VVVEE. The solution was prepared at 1 mM FTY720 and 15 mM C16-VVVEE at pH 7.4, and aged overnight. TEM images show a mixture of nanobelts and filamentous structures.
Figure 10:
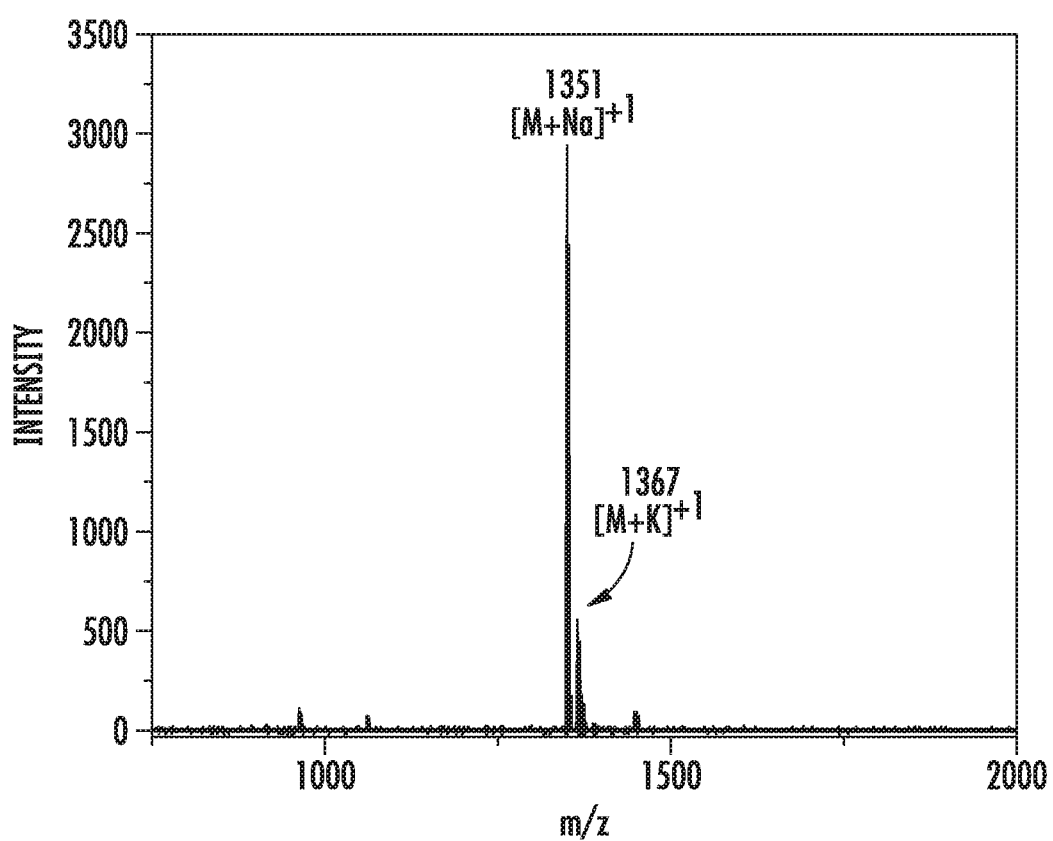
FIG. 10 is a graph of the MALDI mass spectrum data for FTY720-K(C16)-KVVVEE peptide. M=1329 g/mol.
Figure 11:
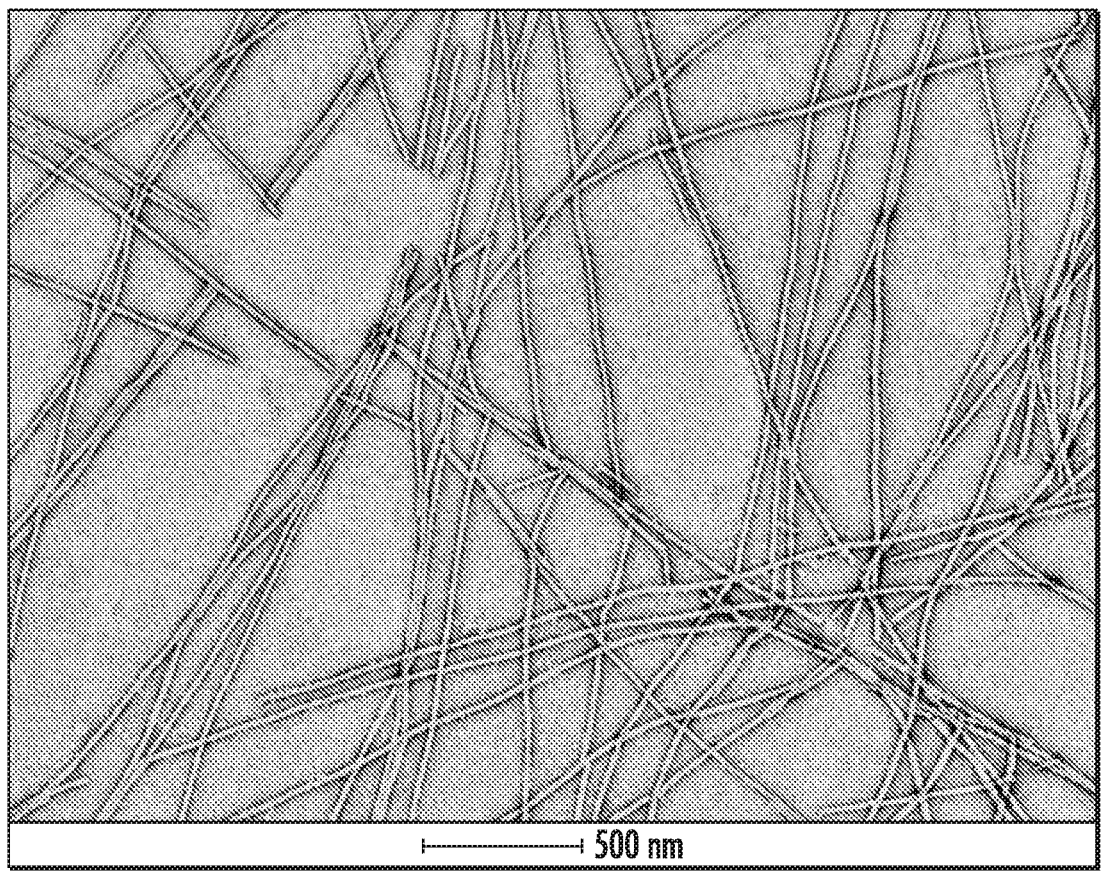
FIG. 11 is a TEM photograph of the drug amphiphile FTY720-K(C16)-KVVVEE. The solution was prepared at 10 mM at pH 7, aged overnight, lyophilized and resuspended in water. TEM images show uniform filamentous structures.

In some embodiments, the drug and hydrophobic tail and be co-assembled into one drug amphiphile molecule, such as the FTY720-K(C16)-KVVVEE peptide depicted in FIG. 4.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the Pep portion of the molecule. A derivative also includes a single or multiple amino acid substitution, deletion and/or addition. Homologues include functionally, structurally or stereochemically similar peptides from the naturally occurring peptide or protein. All such homologs are contemplated by the present invention.

nyl alanine and/or D-isomers of amino acids. A partial list of known non-natural amino acid contemplated herein is shown in Table 1.

TABLE 1

| Non-natural Amino Acids | |
|---|---|
| Non-conventional amino acid | Code |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |

TABLE 1-continued

Non-natural Amino Acids

| Non-conventional amino acid | Code |
|---|---|
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyD)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates small chemical analogs of the naturally occurring Pep moiety. Chemical analogs may not necessarily be derived from the peptides themselves but may share certain conformational similarities. Alternatively, chemical analogs may be specifically designed to mimic certain physiochemical properties of the peptides. Chemical analogs may be chemically synthesized or may be detected following, for example, natural product screening.

In accordance with another embodiment, the present invention provides a pharmaceutical composition comprising a drug amphiphile linked to a TRPM7 receptor antagonist and a pharmaceutically acceptable carrier.

Included within the compounds of the present invention are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include solid compositions such as solid-state carriers or latex beads.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

The choice of carrier will be determined, in part, by the particular pharmaceutical composition, as well as by the particular method used to administer the composition.

Accordingly, there are a variety of suitable formulations of the pharmaceutical composition of the invention.

In accordance with yet another embodiment, the present invention provides a pharmaceutical composition comprising a drug amphiphile linked to a TRPM7 receptor antagonist, a pharmaceutically acceptable carrier and at least one additional biologically active agent.

It will be understood to those of skill in the art that the term "biologically active agent" is any agent capable of affecting the structure or function of the body of a subject or is an agent useful for the treatment or modulation of a disease or condition in a subject suffering therefrom. Examples of therapeutic agents can include any drugs known in the art for treatment of disease indications.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

In a further embodiment, the compositions, methods and uses of the present invention can be used in combination with one or more additional therapeutically active agents which are known to be capable of treating conditions or diseases discussed above. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with an embodiment, the present invention provides a method for treating obesity induced hypertension in a subject suffering therefrom, comprising administering to the subject, an effective amount of a composition comprising a drug amphiphile linked to a TRPM7 receptor antagonist.

In accordance with another embodiment, the present invention provides a method for treating obesity induced hypertension in a subject suffering therefrom, comprising administering to the subject, an effective amount of a pharmaceutical composition comprising a drug amphiphile linked to a TRPM7 receptor antagonist and a pharmaceutically acceptable carrier.

In accordance with yet another embodiment, the present invention provides a method for treating obesity induced hypertension in a subject suffering therefrom, comprising administering to the carotid body of the subject, an effective amount of a composition comprising a drug amphiphile linked to a TRPM7 receptor antagonist.

In accordance with a further embodiment, the present invention provides a method for treating obesity induced hypertension in a subject suffering therefrom, comprising administering to the carotid body of the subject, an effective amount of a pharmaceutical composition comprising a drug amphiphile linked to a TRPM7 receptor antagonist and a pharmaceutically acceptable carrier.

In accordance with an embodiment, the present invention provides a method for treating obstructive sleep apnea in a subject suffering therefrom, comprising administering to the subject an effective amount of a composition comprising a drug amphiphile linked to a TRPM7 receptor antagonist.

In accordance with another embodiment, the present invention provides a method for treating obstructive sleep apnea in a subject suffering therefrom, comprising administering to the subject, an effective amount of a pharmaceutical composition comprising a drug amphiphile linked to a TRPM7 receptor antagonist and a pharmaceutically acceptable carrier.

In accordance with yet another embodiment, the present invention provides a method for treating obstructive sleep apnea in a subject suffering therefrom, comprising administering to the carotid body of the subject, an effective amount of a composition comprising a drug amphiphile linked to a TRPM7 receptor antagonist.

In accordance with a further embodiment, the present invention provides a method for treating obstructive sleep apnea in a subject suffering therefrom, comprising administering to the carotid body of the subject, an effective amount of a pharmaceutical composition comprising a drug amphiphile linked to a TRPM7 receptor antagonist and a pharmaceutically acceptable carrier.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.005 to about 3000 mg/kg body weight of the subject being treated, from about 0.05 to about 300 mg/kg body weight, from about 0.25 mg/kg to about 10 mg/kg, and from about 0.5 mg to about 5 mg/kg body weight. In some embodiments, the dosage when given systemically is about from 1 mg/kg/day to about 10 mg/kg/day, and in some embodiments, about 3 mg/kg/day.

In some embodiments, the compositions of the present invention are applied at or around the carotid body of the subject. In those embodiments, the dosages are in the range of about 0.1 µg to about 5 µg per dose.

As used herein, the terms "effective amount" or "sufficient amount" are equivalent phrases which refer to the amount of a drug amphiphile (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as OSA or hypertension.

Pharmaceutical compositions such as drug amphiphiles, in accordance with the invention are useful for prophylaxis or treatment of a condition. Accordingly, compositions in accordance with the invention are useful as a drug or as information for structural modification of existing compounds, e.g., by rational drug design.

The amount of the drug amphiphile to be administered varies depending upon the manner of administration, the age and body weight of the subject/patient, and with the subject's symptoms and condition. A compound is administered at a dosage that best achieves medical goals with the fewest corresponding side effects.

The pharmaceutical compositions of this invention including biologically active fragments, variants, or analogs thereof, can be administered by certain suitable routes including subcutaneous, intracranial, intracerebral, intrathecal, intraspinal, intravascular, intramuscular and the like.

For example, drug amphiphile according to the invention may be in the form suitable for sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

To prepare such pharmaceutical dosage forms, one or more of the aforementioned drug amphiphiles are intimately admixed with a pharmaceutical carrier according to conventional pharmaceutical compounding techniques. The carrier may take a wide variety of forms depending on the form of preparation desired for administration.

Generally, the amount of administered drug amphiphile of the invention (dosage) will be empirically determined in accordance with information and protocols known in the art.

Drug amphiphile compositions of the invention can comprise various pharmaceutically acceptable salts, ether derivatives, ester derivatives, acid derivatives, and aqueous solubility altering derivatives of the active compound. The present invention can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The biologically active agent which may be added to the drug amphiphiles of the present invention, may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Non-limiting examples of biologically active agents include following: adrenergic blocking agents, calcium channel blockers, angiotensin converting enzyme inhibitors, angiotensin receptor blockers and other anti-hypertensive agents, anti-obesity agents, aldosterone antagonists, diuretics, cardioactive agents, cerebral dilators, coronary dilators, and peripheral vasodilators.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In certain embodiments, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility or for the resulting physical properties of the reagents, the setting or gelling matrix or the set or gelled matrix.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Figure 3A:
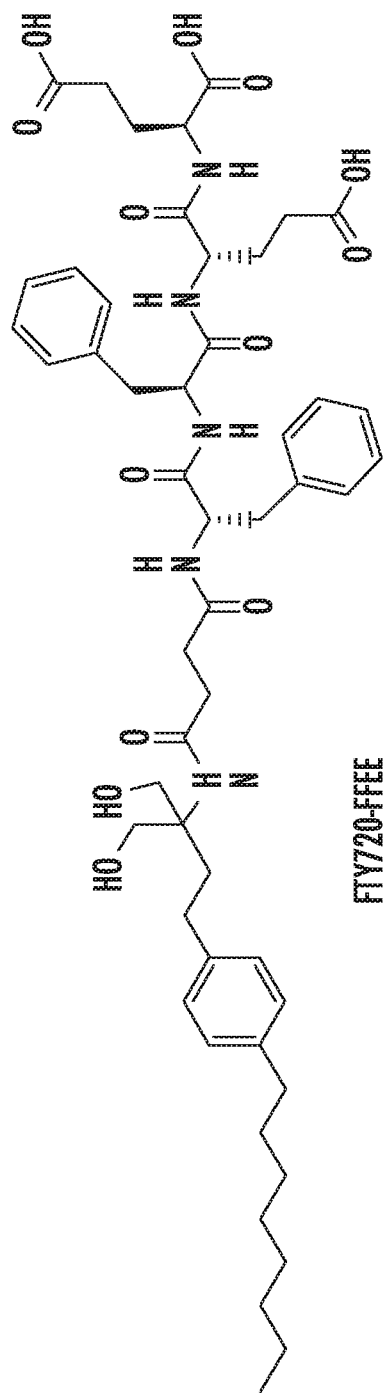
FIG. 3 is a schematic illustration of the design and self-assembly of a representative fingolimod-based drug amphiphiles (DAs) of the present invention into filamentous nanostructures that can further enmesh into hydrogels for long term release of the therapeutic agent.
Figure 3B:
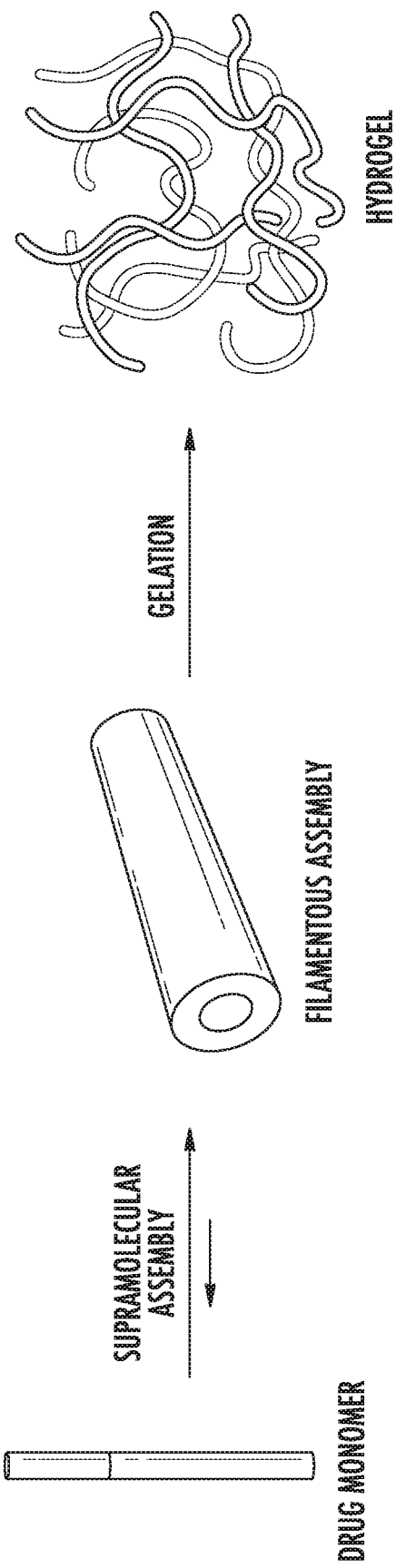

The present inventive fingolimod-based DA compositions are synthesized by the conjugation of a rationally designed hydrophilic peptide segment to the amine group of fingolimod that gives the resulting conjugates overall amphiphilicity, enabling self-assembly (FIG. 3). The conjugation between fingolimod and the peptide is made either via direct covalent bonding between the drug and peptide or via a degradable linker group that allows controlled release in the carotid artery bifurcation.

Figure 12:
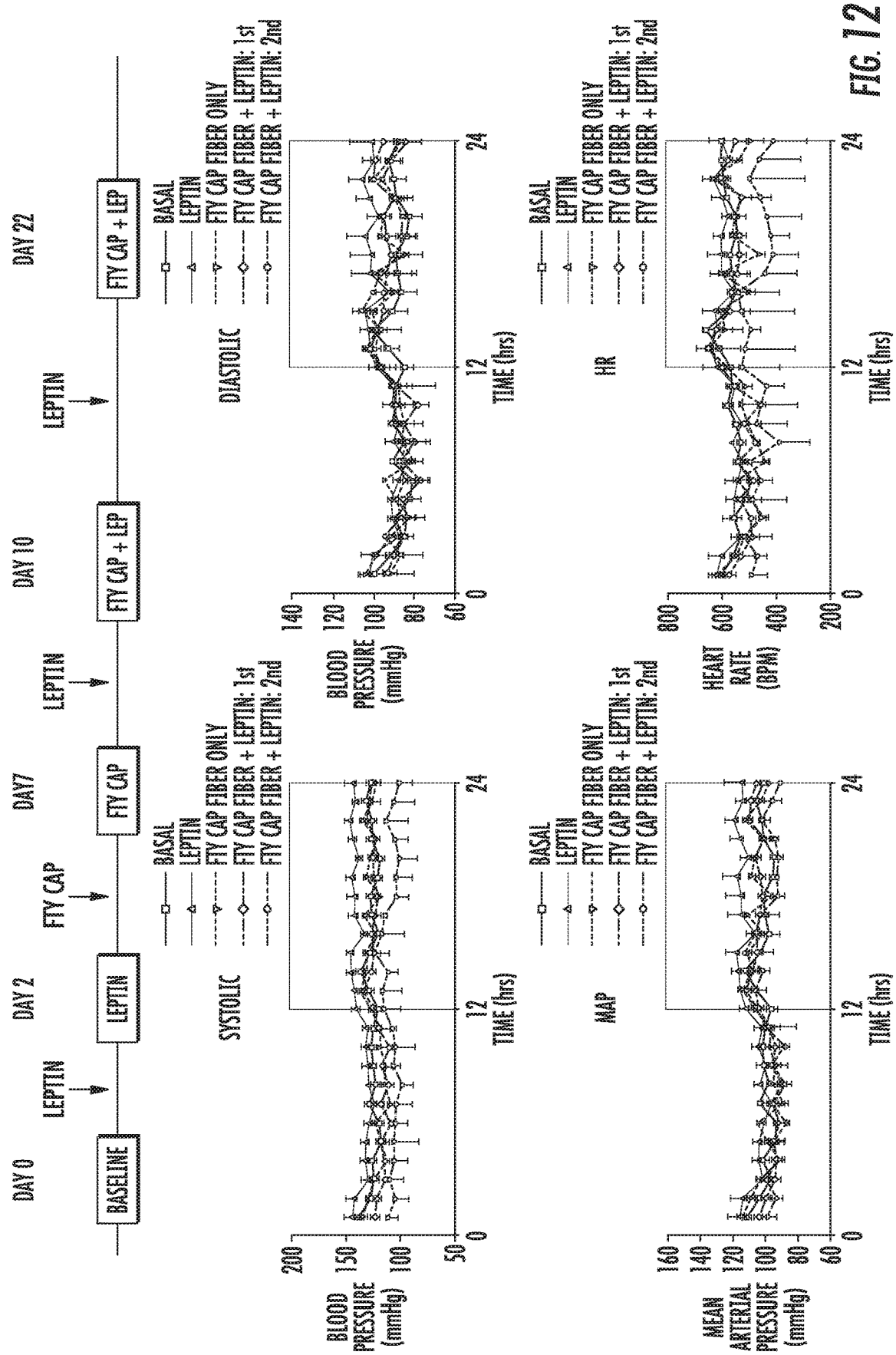
FIG. 12 depicts one experimental design to show the effect of the different FTY720 filamentous nanostructures on blood pressure in mice. A schematic diagram illustrates the dosing protocol of the particular experiment. The graphs depict the systolic pressure (mmHg), diastolic pressure (mmHg), mean arterial pressure (mmHg), and heart rate (BPM) of the mice.

The DA peptide segment is designed with a propensity for β-sheet formation that direct the self-assembly toward the formation of 1D filaments. The assembled DAs possess a 100% drug loading and shield the drug from its environment, protecting it from unwanted degradation. Under appropriate conditions these filaments can then enmesh to give a hydrogel for local delivery of the therapeutic agents.

The purity and identity of the drug amphiphiles was determined through HPLC and mass spectrometric analysis (ESI or MALDI). Nanostructure morphology was assessed using transmission electron microscopy. The internal structure/packing of the assemblies were probed using circular dichroism spectroscopy. Surface charge of the nanoparticles (zeta potential) are evaluated using a Zetasizer (Malvern). To gain further insight into the stability of the produced drug nanoparticles, the critical micellization concentration (CMC), which refers to the concentration above which the molecules self-assemble into nanostructures and below which the molecules exist only in the monomeric state is assessed. The CMC will be determined for each drug nanoparticle, using both surface tension measurement techniques and fluorescent quenching experiments. Dynamic light scattering and circular dichroism measurements serve as complementary methods to provide corroborating evidence for the calculated CMC values of the synthesized self-assembling drug conjugates. In addition to being linked to a rationally designed peptide segment, FTY720 can be co-assembled with a self-assembling peptide conjugate, such as FTY720-K(C16)-KVVVEE. A typical design of the peptide conjugate comprises a hydrophobic chain and a hydrophilic peptide sequence that can spontaneously associate into a supramolecular filament hydrogel under physiological conditions. Mixing of FTY720 with the peptide conjugate in aqueous solution results in co-assembly of the two molecules into the filamentous nanostructure, with the FTY720 sequestered within the nanostructure. Dissociation and/or degradation of the co-assembled FTY720-PA filamentous nanostructures results in sustained release of FTY720 over a long period of time.

Drug release studies and in vitro efficacy evaluation. The FTY720 hydrogel will release the drug over a period of two months on the basis of previous studies with camptothecin. The inventors use well-established protocols to evaluate the release kinetics of the free drug from the self-assembled supramolecular drug hydrogels, and to identify the released products. The release and degradation of the designed drug amphiphile from its hydrogels is evaluated using RP-HPLC. To establish the identity of the released products, LC-MS analysis is performed for each eluted compound. Cytotoxicity of all the synthesized hydrogels is evaluated on a variety of cell lines. Cell viability will be determined using the SRB assay and expressed as a percentage of the untreated control cells. Data is fitted using the sigmoid or Hill equation curve analysis functions to obtain the respective $IC_{50}$ value for each drug amphiphile.

Blood pressure telemetry (FIG. 2) and sleep studies in mice. Dr. Polotsky, one of the inventors, previously demonstrated that obese mice develop OSA similar to humans.[84]

Study Design: Male and female C57BL/6J mice on a high fat diet (HFD, TD 03584, Teklad Wis., 5.4 kcal/g, 35.2% fat, 58.4% of kcal from fat) with diet induced obesity (DIO) weighing at least 45 g (males) or 38-40 g (females) and mice on a chow diet (20-25 g of body weight) will undergo blood pressure telemetry implantation into the aorta via the left femoral artery and head mount of EMG and EEG electrodes for sleep study recording. After 1 week recovery blood pressure will be recorded for 24 hours and sleep study will be performed (FIG. 2). Subsequently FTY720 hydrogel or control hydrogel will be applied to the carotid artery bifurcation (CB) area. 24 hour blood pressure recordings and sleep studies will be performed 1 week, 2 weeks, 4 weeks, 6 weeks and 8 weeks after fingolimod or placebo application. We will measure FTY720 plasma levels and CBC to assure safety.

In an experiment, male C57BL/6J mice (n=3) had blood pressure telemetry implanted in the descending aorta via the left femoral artery followed by one-week recovery. Then blood pressure was measured at baseline (Day 0). The leptin osmotic pump was implanted SC to deliver 120 μg/day of the hormone, which increased leptin levels to 40-50 ng/ml which corresponded to plasma leptin levels in severely obese mice. Blood pressure measured after 2 days of leptin infusion (Day 2) followed by removal of the osmotic pump. On Day 5, the carotid artery bifurcation was exposed and co-assembled FTY720-PA filamentous nanostructures were applied bilaterally (5 μg/side). Blood pressure was measured on Day 7 demonstrating an effect of FTY720 in the absence of leptin. The leptin osmotic pump was reinserted on Day 9 and blood pressure was measured after two days of leptin infusion on Day 11. The pump was removed on Day 12 and reinserted on Day 20 followed by blood pressure measurement on Day 22. The experiment demonstrates that FTY720-PA is effective in controlling leptin-induced hypertension 17 days after implantation. Given the different in FTY720 metabolism between mice and humans (half-life 9 hours versus 7 days respectively), our data suggest that FTY720-PA nanostructures will effective long-term treatment of leptin-induced hypertension in obese patients (FIG. 12).

Leptin increased mean arteria blood pressure by 13±6 mm Hg and this effect was abolished by FTY720. To reject the null hypothesis that "FTY720 does not decrease blood pressure," with 90% power with 6 mice per group. Allowing 10% attrition rate, it will require 28 male (14 DIO and 14 lean) and 28 female C57BL/6J mice (14 DIO and 14 lean).

It is anticipated that mice on a high fat diet and high circulating leptin levels (40-50 ng/ml compared to 1-2 ng/ml in lean mice) will develop hypertension 4 and OSA. FTY720 hydrogel will abolish both hypertension and OSA in obese mice, whereas it will not have an effect on lean mice, which have normal blood pressure and breathing at baseline. It is anticipated that the effects will be similar in male and female mice. It is anticipated low plasma FTY levels and normal lymphocyte count (no lymphopenia).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Hubert, H. B., M. Feinleib, P. M. McNamara, and W. P. Castelli. 1983. Obesity as an independent risk factor for cardiovascular disease: a 26-year follow-up of participants in the Framingham Heart Study. *Circulation* 67:968-977.
2. Van Gaal, L. F., I. L. Mertens, and C. E. De Block. 2006. Mechanisms linking obesity with cardiovascular disease. *Nature* 444:875-880.
3. Hall, J. E., A. A. da Silva, J. M. do Carmo, J. Dubinion, S. Hamza, S. Munusamy, G. Smith, and D. E. Stec. 2010. Obesity-induced hypertension: role of sympathetic nervous system, leptin, and melanocortins. *J. Biol. Chem.* 285:17271-17276.
4. Rahmouni, K., D. A. Morgan, G. M. Morgan, A. L. Mark, and W. G. Haynes. 2005. Role of selective leptin resistance in diet-induced obesity hypertension. *Diabetes* 54:2012-2018.
5. Rahmouni, K., M. L. Correia, W. G. Haynes, and A. L. Mark. 2005. Obesity-associated hypertension: new insights into mechanisms. *Hypertension* 45:9-14.
6. Young, T., M. Palta, J. Dempsey, J. Skatrud, S. Weber, and S. Badr. 1993. The occurrence of sleep-disordered breathing among middle-aged adults. *N. Engl. J Med* 328:1230-1235.
7. Vgontzas, A. N., D. A. Papanicolaou, E. O. Bixler, K. Hopper, A. Lotsikas, H. M. Lin, A. Kales, and G. P. Chrousos. 2000. Sleep apnea and daytime sleepiness and fatigue: relation to visceral obesity, insulin resistance, and hypercytokinemia [see comments]. *J Clin. Endocrinol. Metab* 85:1151-1158.
8. Punjabi, N. M., J. D. Sorkin, L. I. Katzel, A. P. Goldberg, A. R. Schwartz, and P. L. Smith. 2002. Sleep-disordered breathing and insulin resistance in middle-aged and overweight men. *Am. J. Respir. Crit Care Med.* 165:677-682.
9. Young, T., P. E. Peppard, and D. J. Gottlieb. 2002. Epidemiology of obstructive sleep apnea: a population health perspective. *Am J Respir Crit Care Med* 165:1217-1239.
10. Tufik, S., R. Santos-Silva, J. A. Taddei, and L. R. Bittencourt. 2010. Obstructive sleep apnea syndrome in the Sao Paulo Epidemiologic Sleep Study. *Sleep Med.* 11:441-446.
11. Asferg, C., R. Mogelvang, A. Flyvbjerg, J. Frystyk, J. S. Jensen, J. L. Maxon, M. Appleyard, G. B. Jensen, and J. Jeppesen. 2010. Leptin, not adiponectin, predicts hypertension in the Copenhagen City Heart Study. *Am. J. Hypertens.* 23:327-333.
12. Shankar, A. and J. Xiao. 2010. Positive relationship between plasma leptin level and hypertension. *Hypertension* 56:623-628.
13. Mark, A. L., M. L. Correia, K. Rahmouni, and W. G. Haynes. 2002. Selective leptin resistance: a new concept in leptin physiology with cardiovascular implications. *J. Hypertens.* 20:1245-1250.
14. Samuelsson, A. M., J. Clark, O. Rudyk, M. J. Shattock, S. E. Bae, T. South, J. Pombo, K. Redington, E. Uppal, C. W. Coen, et al. 2013. Experimental hyperleptinemia in neonatal rats leads to selective leptin responsiveness, hypertension, and altered myocardial function. *Hypertension* 62:627-633.

15. Spiegelman, B. M. and J. S. Flier. 2001. Obesity and the regulation of energy balance. *Cell* 104:531-543.
16. Buyse, B., N. Markous, M. Cauberghs, K. R. Van, E. Muls, and M. Demedts. 2003. Effect of obesity and/or sleep apnea on chemosensitivity: differences between men and women. *Respir. Physiol Neurobiol.* 134:13-22.
17. Chapman, K. R., H. S. Himal, and A. S. Rebuck. 1990. Ventilatory responses to hypercapnia and hypoxia in patients with eucapnic morbid obesity before and after weight loss. *Clin. Sci. (Lond)* 78:541-545.
18. Trombetta, I. C., C. Maki-Nunes, E. Toschi-Dias, M. J. Alves, M. U. Rondon, F. X. Cepeda, L. F. Drager, A. M. Braga, G. Lorenzi-Filho, and C. E. Negrao. 2013. Obstructive sleep apnea is associated with increased chemoreflex sensitivity in patients with metabolic syndrome. *Sleep* 36:41-49.
19. Pialoux, V., P. J. Hanly, G. E. Foster, J. V. Brugniaux, A. E. Beaudin, S. E. Hartmann, M. Pun, C. T. Duggan, and M. J. Poulin. 2009. Effects of exposure to intermittent hypoxia on oxidative stress and acute hypoxic ventilatory response in humans. *Am. J. Respir. Crit Care Med.* 180:1002-1009.
20. Younes, M., M. Ostrowski, R. Atkar, J. Laprairie, A. Siemens, and P. Hanly. 2007. Mechanisms of breathing instability in patients with obstructive sleep apnea. *J. Appl. Physiol* (1985.) 103:1929-1941.
21. Mateika, J. H. 2015. The role of high loop gain induced by intermittent hypoxia in the pathophysiology of obstructive sleep apnea. *Sleep Med. Rev.* 22:1-2.
22. Younes, M. 2014. CrossTalk proposal: elevated loop gain is a consequence of obstructive sleep apnoea. *J. Physiol* 592:2899-2901.
23. Nieto, F. J., T. B. Young, B. K. Lind, E. Shahar, J. M. Samet, S. Redline, R. B. D'Agostino, A. B. Newman, M. D. Lebowitz, and T. G. Pickering. 2000. Association of sleep-disordered breathing, sleep apnea, and hypertension in a large community-based study. Sleep Heart Health Study [see comments]. *JAMA* 283:1829-1836.
24. Peppard, P. E., T. Young, M. Palta, and J. Skatrud. 2000. Prospective study of the association between sleep-disordered breathing and hypertension. *N. Engl. J Med* 342:1378-1384.
25. Norman, D., J. S. Loredo, R. A. Nelesen, S. Ancoli-Israel, P. J. Mills, M. G. Ziegler, and J. E. Dimsdale. 2006. Effects of continuous positive airway pressure versus supplemental oxygen on 24-hour ambulatory blood pressure. *Hypertension* 47:840-845.
26. Pedrosa, R. P., L. F. Drager, C. C. Gonzaga, M. G. Sousa, L. K. de Paula, A. C. Amaro, C. Amodeo, L. A. Bortolotto, E. M. Krieger, T. D. Bradley, et al. 2011. Obstructive sleep apnea: the most common secondary cause of hypertension associated with resistant hypertension. *Hypertension* 58:811-817.
27. Prabhakar, N. R. 2013. Sensing hypoxia: physiology, genetics and epigenetics. *J Physiol* 591:2245-2257.
28. Morgan, B. J., R. Adrian, M. L. Bates, J. M. Dopp, and J. A. Dempsey. 2014. Quantifying hypoxia-induced chemoreceptor sensitivity in the awake rodent. *J. Appl. Physiol* (1985.) 117:816-824.
29. Nurse, C. A. and N. A. Piskuric. 2013. Signal processing at mammalian carotid body chemoreceptors. *Semin. Cell Dev. Biol.* 24:22-30.
30. Prabhakar, N. R., G. K. Kumar, and Y. J. Peng. 2012. Sympatho-adrenal activation by chronic intermittent hypoxia. *J Appl. Physiol* 113:1304-1310.
31. Silva, A. Q. and A. M. Schreihofer. 2011. Altered sympathetic reflexes and vascular reactivity in rats after exposure to chronic intermittent hypoxia. *J Physiol* 589:1463-1476.
32. Gonzalez-Martin, M. C., M. V. Vega-Agapito, S. V. Conde, J. Castaneda, R. Bustamante, E. Olea, F. Perez-Vizcaino, C. Gonzalez, and A. Obeso. 2011. Carotid body function and ventilatory responses in intermittent hypoxia. Evidence for anomalous brainstem integration of arterial chemoreceptor input. *J. Cell Physiol* 226:1961-1969.
33. Ribeiro, M. J., J. F. Sacramento, C. Gonzalez, M. P. Guarino, E. C. Monteiro, and S. V. Conde. 2013. Carotid body denervation prevents the development of insulin resistance and hypertension induced by hypercaloric diets. *Diabetes* 62:2905-2916.
34. Peng, Y. J., J. L. Overholt, D. Kline, G. K. Kumar, and N. R. Prabhakar. 2003. Induction of sensory long-term facilitation in the carotid body by intermittent hypoxia: implications for recurrent apneas. *Proc. Natl. Acad. Sci. U.S.A* 100:10073-10078.
35. Peng, Y. J., J. Rennison, and N. R. Prabhakar. 2004. Intermittent hypoxia augments carotid body and ventilatory response to hypoxia in neonatal rat pups. *J Appl. Physiol* 97:2020-2025.
36. Peng, Y. J., G. Yuan, D. Ramakrishnan, S. D. Sharma, M. Bosch-Marce, G. K. Kumar, G. L. Semenza, and N. R. Prabhakar. 2006. Heterozygous HIF-1 {alpha} deficiency impairs carotid body-mediated systemic responses and reactive oxygen species generation in mice exposed to intermittent hypoxia. *J. Physiol* 577:705-716.
37. Peng, Y. J., G. Yuan, F. J. Jacono, G. K. Kumar, and N. R. Prabhakar. 2006. 5-HT evokes sensory long-term facilitation of rodent carotid body via activation of NADPH oxidase. *J. Physiol* 576:289-295.
38. Peng, Y. J., J. Nanduri, G. Yuan, N. Wang, E. Deneris, S. Pendyala, V. Natarajan, G. K. Kumar, and N. R. Prabhakar. 2009. NADPH oxidase is required for the sensory plasticity of the carotid body by chronic intermittent hypoxia. *J Neurosci.* 29:4903-4910.
39. Prabhakar, N. R., T. E. Dick, J. Nanduri, and G. K. Kumar. 2007. Systemic, cellular and molecular analysis of chemoreflex-mediated sympathoexcitation by chronic intermittent hypoxia. *Exp. Physiol* 92:39-44.
40. Prabhakar, N. R., G. K. Kumar, and J. Nanduri. 2010. Intermittent hypoxia augments acute hypoxic sensing via HIF-mediated ROS. *Respir Physiol Neurobiol.* 174:230-234.
41. Prabhakar, N. R. 2011. Sensory plasticity of the carotid body: role of reactive oxygen species and physiological significance. *Respir Physiol Neurobiol.* 178:375-380.
42. Bao, G., N. Metreveli, R. Li, A. Taylor, and E. C. Fletcher. 1997. Blood pressure response to chronic episodic hypoxia: role of the sympathetic nervous system. *J. Appl. Physiol* 83:95-101.
43. Marcus, N. J., Y. L. Li, C. E. Bird, H. D. Schultz, and B. J. Morgan. 2010. Chronic intermittent hypoxia augments chemoreflex control of sympathetic activity: role of the angiotensin II type 1 receptor. *Respir Physiol Neurobiol.* 171:36-45.
44. Shirahata, M., W. Y. Tang, M. K. Shin, and V. Y. Polotsky. 2015. Is the Carotid Body a Metabolic Monitor? *Adv. Exp. Med. Biol.* 860:153-159.
45. Aarts, M., K. lihara, W. L. Wei, Z. G. Xiong, M. Arundine, W. Cerwinski, J. F. MacDonald, and M. Tymianski. 2003. A key role for TRPM7 channels in anoxic neuronal death. *Cell* 115:863-877.

46. Sun, H. S., M. F. Jackson, L. J. Martin, K. Jansen, L. Teves, H. Cui, S. Kiyonaka, Y. Mori, M. Jones, J. P. Forder, et al. 2009. Suppression of hippocampal TRPM7 protein prevents delayed neuronal death in brain ischemia. *Nat. Neurosci.* 12:1300-1307.
47. Mori, Y., N. Takahashi, 0. K. Polat, T. Kurokawa, N. Takeda, and M. Inoue. 2015. Redox-sensitive transient receptor potential channels in oxygen sensing and adaptation. *Pflugers Arch.*
48. Lublin, F., D. H. Miller, M. S. Freedman, B. A. Cree, J. S. Wolinsky, H. Weiner, C. Lubetzki, H. P. Hartung, X. Montalban, B. M. Uitdehaag, et al. 2016. Oral fingolimod in primary progressive multiple sclerosis (INFORMS): a phase 3, randomised, double-blind, placebo-controlled trial. *Lancet.*
49. Kappos, L., E. W. Radue, P. O'Connor, C. Polman, R. Hohlfeld, P. Calabresi, K. Selmaj, C. Agoropoulou, M. Leyk, L. Zhang-Auberson, et al. 2010. A placebo-controlled trial of oral fingolimod in relapsing multiple sclerosis. *N. Engl. J Med.* 362:387-401.
50. Cohen, J. A., F. Barkhof, G. Comi, H. P. Hartung, B. O. Khatri, X. Montalban, J. Pelletier, R. Capra, P. Gallo, G. Izquierdo, et al. 2010. Oral fingolimod or intramuscular interferon for relapsing multiple sclerosis. *N. Engl. J. Med* 362:402-415.
51. Comi, G., P. O'Connor, X. Montalban, J. Antel, E. W. Radue, G. Karlsson, H. Pohlmann, S. Aradhye, and L. Kappos. 2010. Phase II study of oral fingolimod (FTY720) in multiple sclerosis: 3-year results. *Mult. Scler.* 16:197-207.
52. Chubanov, V., S. Schafer, S. Ferioli, and T. Gudermann. 2014. Natural and Synthetic Modulators of the TRPM7 Channel. *Cells* 3:1089-1101.
53. Qin, X., Z. Yue, B. Sun, W. Yang, J. Xie, E. Ni, Y. Feng, R. Mahmood, Y. Zhang, and L. Yue. 2013. Sphingosine and FTY720 are potent inhibitors of the transient receptor potential melastatin 7 (TRPM7) channels. *Br. J. Pharmacol.* 168:1294-1312.
54. Ogden, C. L., M. D. Carroll, and K. M. Flegal. 2014. Prevalence of obesity in the United States. *JAMA* 312:189-190.
55. Adams, K. F., A. Schatzkin, T. B. Harris, V. Kipnis, T. Mouw, R. Ballard-Barbash, A. Hollenbeck, and M. F. Leitzmann. 2006. Overweight, obesity, and mortality in a large prospective cohort of persons 50 to 71 years old. *N. Engl. J Med.* 355:763-778.
56. Dixon, A. E., R. E. Pratley, P. M. Forgione, D. A. Kaminsky, L. A. Whittaker-Leclair, L. A. Griffes, J. Garudathri, D. Raymond, M. E. Poynter, J. Y. Bunn, et al. 2011. Effects of obesity and bariatric surgery on airway hyperresponsiveness, asthma control, and inflammation. *J. Allergy Clin. Immunol.* 128:508-515.
57. Schwartz, A. R., A. R. Gold, N. Schubert, A. Stryzak, R. A. Wise, S. Permutt, and P. L. Smith. 1991. Effect of weight loss on upper airway collapsibility in obstructive sleep apnea. *Am Rev. Respir. Dis.* 144:494-498.
58. Smith, P. L., A. R. Gold, D. A. Meyers, E. F. Haponik, and E. R. Bleecker. 1985. Weight loss in mildly to moderately obese patients with obstructive sleep apnea. *Ann. Intern Med* 103:850-855.
59. Tuomilehto, J., J. Lindstrom, J. G. Eriksson, T. T. Valle, H. Hamalainen, P. Ilanne-Parikka, S. Keinanen-Kiukaanniemi, M. Laakso, A. Louheranta, M. Rastas, et al. 2001. Prevention of type 2 diabetes mellitus by changes in lifestyle among subjects with impaired glucose tolerance. *N. Engl. J Med* 344:1343-1350.
60. Juonala, M., C. G. Magnussen, G. S. Berenson, A. Venn, T. L. Burns, M. A. Sabin, S. R. Srinivasan, S. R. Daniels, P. H. Davis, W. Chen, et al. 2011. Childhood adiposity, adult adiposity, and cardiovascular risk factors. *N. Engl. J. Med* 365:1876-1885.
61. Shashaj, B., G. Bedogni, M. P. Graziani, A. E. Tozzi, M. L. DiCorpo, D. Morano, L. Tacconi, P. Veronelli, B. Contoli, and M. Manco. 2014. Origin of cardiovascular risk in overweight preschool children: a cohort study of cardiometabolic risk factors at the onset of obesity. *JAMA Pediatr.* 168:917-924.
62. Ford, E. S., W. H. Giles, and W. H. Dietz. 2002. Prevalence of the metabolic syndrome among US adults: findings from the third National Health and Nutrition Examination Survey. *JAMA* 287:356-359.
63. Williams, P. T., S. P. Fortmann, R. B. Terry, S. C. Garay, K. M. Vranizan, N. Ellsworth, and P. D. Wood. 1987. Associations of dietary fat, regional adiposity, and blood pressure in men. *JAMA* 257:3251-3256.
64. Franks, P. W., R. L. Hanson, W. C. Knowler, M. L. Sievers, P. H. Bennett, and H. C. Looker. 2010. Childhood obesity, other cardiovascular risk factors, and premature death. *N. Eng. J Med* 362:485-493.
65. Janik, M., M. D. Cham, M. I. Ross, Y. Wang, N. Codella, J. K. Min, M. R. Prince, S. Manoushagian, P. M. Okin, R. B. Devereux, et al. 2008. Effects of papillary muscles and trabeculae on left ventricular quantification: increased impact of methodological variability in patients with left ventricular hypertrophy. *J. Hypertens.* 26:1677-1685.
66. Marin, J. M., S. J. Carrizo, E. Vicente, and A. G. Agusti. 2005. Long-term cardiovascular outcomes in men with obstructive sleep apnoea-hypopnoea with or without treatment with continuous positive airway pressure: an observational study. *Lancet* 365:1046-1053.
67. Punjabi, N. M., B. S. Caffo, J. L. Goodwin, D. J. Gottlieb, A. B. Newman, G. T. O'Connor, D. M. Rapoport, S. Redline, H. E. Resnick, J. A. Robbins, et al. 2009. Sleep-disordered breathing and mortality: a prospective cohort study. *PLoS. Med* 6:e1000132.
68. Young, T., L. Finn, P. E. Peppard, M. Szklo-Coxe, D. Austin, F. J. Nieto, R. Stubbs, and K. M. Hla. 2008. Sleep disordered breathing and mortality: eighteen-year follow-up of the Wisconsin sleep cohort. *Sleep* 31:1071-1078.
69. Narkiewicz, K., P. J. van de Borne, R. L. Cooley, M. E. Dyken, and V. K. Somers. 1998. Sympathetic activity in obese subjects with and without obstructive sleep apnea. *Circulation* 98:772-776.
70. Narkiewicz, K., V. K. Somers, L. Mos, M. Kato, V. Accurso, and P. Palatini. 1999. An independent relationship between plasma leptin and heart rate in untreated patients with essential hypertension. *J Hypertens.* 17:245-249.
71. Grassi, G., A. Facchini, F. Q. Trevano, R. Dell'Oro, F. Arenare, F. Tana, G. Bolla, A. Monzani, M. Robuschi, and G. Mancia. 2005. Obstructive sleep apnea-dependent and -independent adrenergic activation in obesity. *Hypertension* 46:321-325.
72. Sanchez-de-la-Torre, M., A. Khalyfa, A. Sanchez-de-la-Torre, M. Martinez-Alonso, M. A. Martinez-Garcia, A. Barcelo, P. Lloberes, F. Campos-Rodriguez, F. Capote, M. J. Diaz-de-Atauri, et al. 2015. Precision Medicine in Patients With Resistant Hypertension and Obstructive Sleep Apnea: Blood Pressure Response to Continuous Positive Airway Pressure Treatment. *J. Am. Coll. Cardiol.* 66:1023-1032.

73. Rao, A., V. Pandya, and A. Whaley-Connell. 2015. Obesity and insulin resistance in resistant hypertension: implications for the kidney. *Adv. Chronic. Kidney Dis.* 22:211-217.
74. Brambilla, G., M. Bombelli, G. Seravalle, R. Cifkova, S. Laurent, K. Narkiewicz, R. Facchetti, J. Redon, G. Mancia, and G. Grassi. 2013. Prevalence and clinical characteristics of patients with true resistant hypertension in central and Eastern Europe: data from the BP-CARE study. *J. Hypertens.* 31:2018-2024.
75. Roberie, D. R. and W. J. Elliott. 2012. What is the prevalence of resistant hypertension in the United States? *Curr. Opin. Cardiol.* 27:386-391.
76. Cheetham, A. G., P. Zhang, Y. A. Lin, R. Lin, and H. Cui. 2014. Synthesis and Self-Assembly of a Mikto-Arm Star Dual Drug Amphiphile Containing both Paclitaxel and Camptothecin. *J. Mater. Chem. B Mater. Biol. Med.* 2:7316-7326.
77. Cheetham, A. G., P. Zhang, Y. A. Lin, L. L. Lock, and H. Cui. 2013. Supramolecular nanostructures formed by anticancer drug assembly. *J. Am. Chem. Soc.* 135:2907-2910.
78. Chen, Z., P. Zhang, A. G. Cheetham, J. H. Moon, J. W. Moxley, Jr., Y. A. Lin, and H. Cui. 2014. Controlled release of free doxorubicin from peptide-drug conjugates by drug loading. *J. Control Release* 191:123-130.
79. Zhang, P., A. G. Cheetham, L. L. Lock, and H. Cui. 2013. Cellular uptake and cytotoxicity of drug-peptide conjugates regulated by conjugation site. *Bioconjug. Chem.* 24:604-613.
80. Zhang, P., L. L. Lock, A. G. Cheetham, and H. Cui. 2014. Enhanced cellular entry and efficacy of tat conjugates by rational design of the auxiliary segment. *Mol. Pharm.* 11:964-973.
81. Lin, R., A. G. Cheetham, P. Zhang, Y. A. Lin, and H. Cui. 2013. Supramolecular filaments containing a fixed 41% paclitaxel loading. *Chem. Commun. (Camb.)* 49:4968-4970.
82. Lin, Y. A., A. G. Cheetham, P. Zhang, Y. C. Ou, Y. Li, G. Liu, D. Hermida-Merino, I. W. Hamley, and H. Cui. 2014. Multiwalled nanotubes formed by catanionic mixtures of drug amphiphiles. *ACS Nano.* 8:12690-12700.
83. Pho, H., A. B. Hernandez, R. S. Arias, E. B. Leitner, K. S. Van, J. P. Kirkness, H. Schneider, P. L. Smith, V. Y. Polotsky, and A. R. Schwartz. 2016. The effect of leptin replacement on sleep-disordered breathing in the leptin-deficient ob/ob mouse. *J. Appl. Physiol* (1985.) 120:78-86.
84. Yao, Q., H. Pho, J. Kirkness, E. E. Ladenheim, S. Bi, T. H. Moran, D. D. Fuller, A. R. Schwartz, and V. Y. Polotsky. 2016. Localizing Effects of Leptin on Upper Airway and Respiratory Control during Sleep. *Sleep* 39:1097-1106.

The invention claimed is:

1. A composition comprising a drug amphiphile comprising a transient receptor potential melastatin 7 (TRPM7) receptor antagonist and a pharmaceutically acceptable carrier, wherein the drug amphiphile has one of the following formulas:

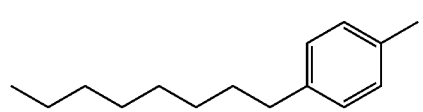

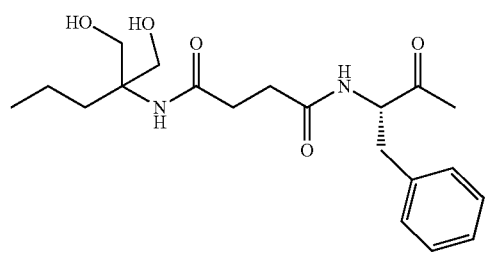

-continued

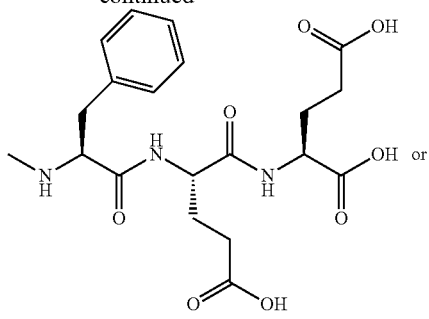

FTY720•FFEE

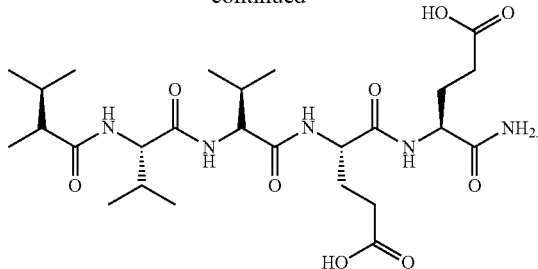

2. The composition of claim 1, which further comprises at least one additional biologically active agent.

3. A method for treating obesity induced hypertension in a subject suffering therefrom comprising administering to the subject an effective amount of the composition of claim 1.

4. A method for treating obstructive sleep apnea in a subject suffering therefrom comprising administering to the subject an effective amount of the composition of claim 1.

* * * * *

UNITED STATES PATENT AND TRADEMARK OFFICE
CERTIFICATE OF CORRECTION

| | | |
|---|---|---|
| PATENT NO. | : 11,229,614 B2 | Page 1 of 3 |
| APPLICATION NO. | : 16/955626 | |
| DATED | : January 25, 2022 | |
| INVENTOR(S) | : Vsevolod Polotsky et al. | |

It is certified that error appears in the above-identified patent and that said Letters Patent is hereby corrected as shown below:

In the Claims

Claim 1, Columns 27-30, the formulas are broken up in three separate parts and reads:

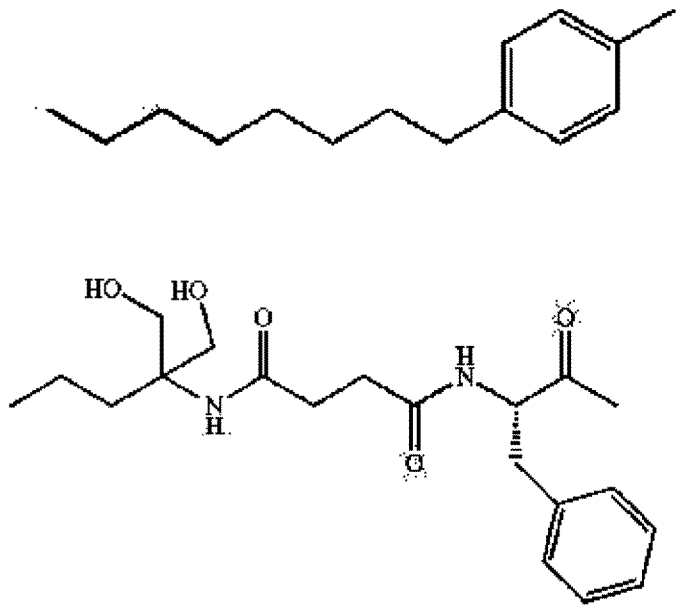

"

Signed and Sealed this
Eleventh Day of April, 2023

*Katherine Kelly Vidal*

Katherine Kelly Vidal
*Director of the United States Patent and Trademark Office*

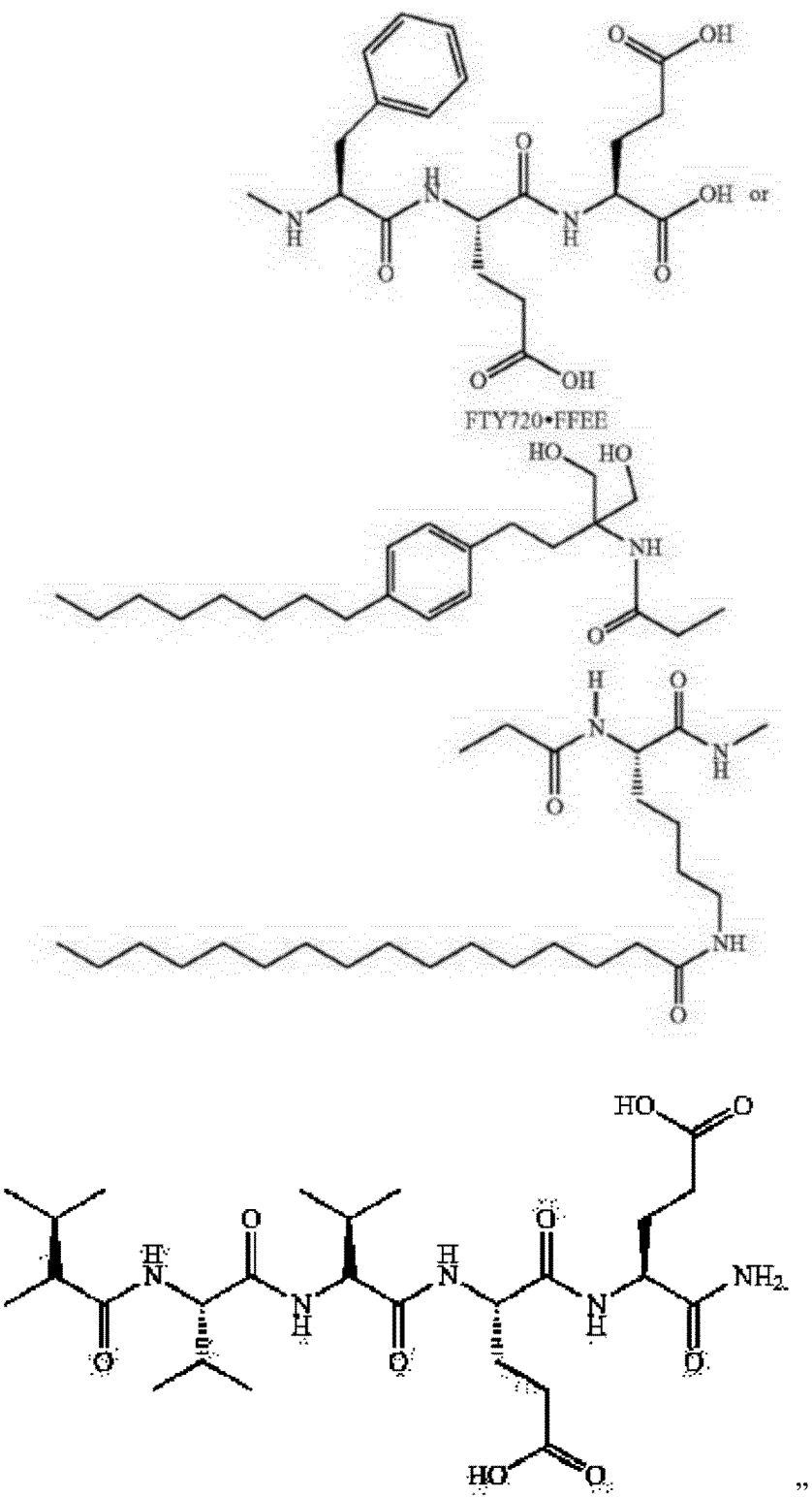

CERTIFICATE OF CORRECTION (continued)  Page 3 of 3
U.S. Pat. No. 11,229,614 B2

Whereas it should read:

" 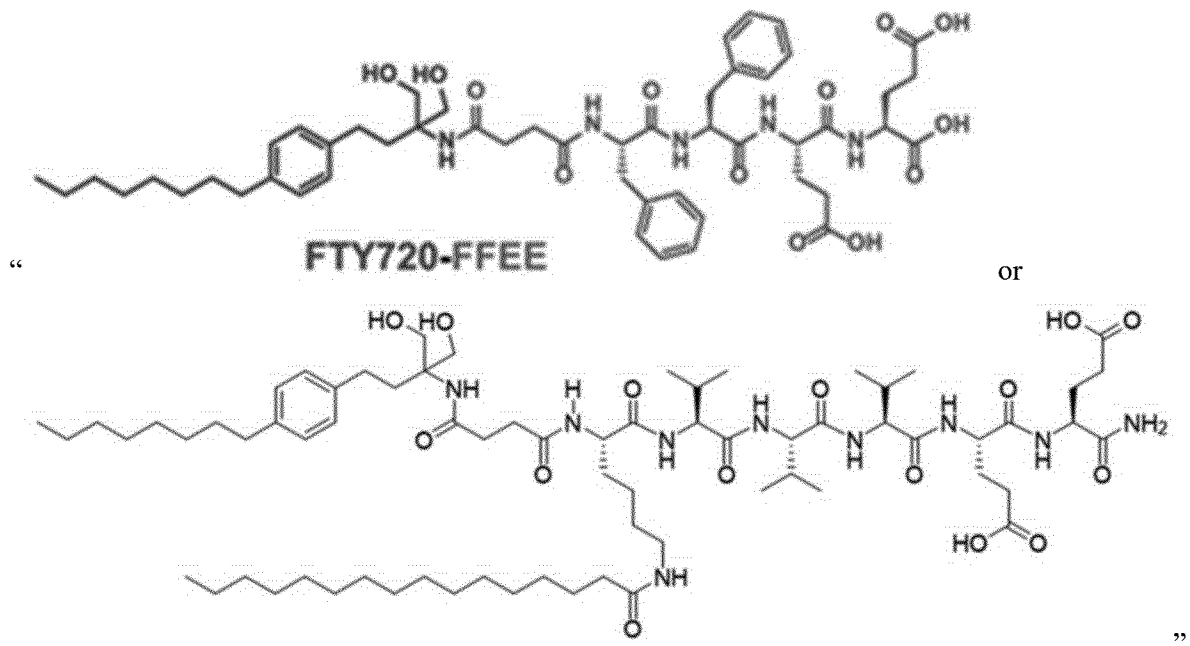 or

"